(12) United States Patent
Vatta et al.

(10) Patent No.: US 8,906,628 B2
(45) Date of Patent: *Dec. 9, 2014

(54) **NUCLEIC ACID AMPLIFICATION METHODS FOR SPECIFIC DETECTION OF *E. COLI* O157:H7 WITHOUT CO-DETECTION OF *E. COLI* O55:H7**

(71) Applicant: Life Technologies Corporation, Carlsbad, CA (US)

(72) Inventors: Paolo Vatta, San Mateo, CA (US); Olga Petrauskene, San Carlos, CA (US); Manohar Furtado, San Ramon, CA (US); Pius Brzoska, Woodside, CA (US); Lily Wong, San Mateo, CA (US); Melissa Barker, Gilroy, CA (US); Craig Cummings, Pacifica, CA (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/870,779

(22) Filed: Apr. 25, 2013

(65) Prior Publication Data

US 2013/0236896 A1 Sep. 12, 2013

Related U.S. Application Data

(63) Continuation of application No. 12/780,707, filed on May 14, 2010, now Pat. No. 8,445,209.

(60) Provisional application No. 61/178,931, filed on May 15, 2009.

(51) Int. Cl.
*C12Q 1/68* (2006.01)
*C12P 19/34* (2006.01)

(52) U.S. Cl.
CPC ..................................... *C12Q 1/689* (2013.01)
USPC .......................................... 435/6.12; 435/91.2

(58) Field of Classification Search
USPC ................................................ 435/6.12, 91.2
See application file for complete search history.

(56) References Cited

U.S. PATENT DOCUMENTS

| 5,654,417 | A | 8/1997 | Tarr et al. |
| 5,747,257 | A | 5/1998 | Jensen |
| 6,365,723 | B1 | 4/2002 | Blattner et al. |
| 8,445,209 | B2 | 5/2013 | Vatta et al. |
| 2004/0248148 | A1 | 12/2004 | Horgen et al. |

FOREIGN PATENT DOCUMENTS

| EP | 1260592 | 11/2002 |
| FR | 2784117 | 4/2000 |
| JP | 2002355074 | 12/2002 |
| WO | WO99/04039 | 1/1999 |
| WO | WO00/77247 | 12/2000 |
| WO | WO2010/132832 | 11/2010 |

OTHER PUBLICATIONS

Ibekwe et al., "Multiplex Fluorogenic Real-Time PCR for Detection and Quantification of *Escherichia coli* O157:H7 in Dairy Wastewater Wetlands", *Applied and Environmental Microbiology*, vol. 68, No. 10, Oct. 2002, 4853-4862.
Intl Application No. PCTUS2010034998, International Search Report and Written Opinion Received mailed Aug. 4, 2010.
Jothikumar et al., "Rapid Detection of *Escherichia coli* O157:H7 with Multiplex Real-Time PCR Assays", *Applied and Environmental Microbiology*, vol. 68, No. 6, Jun. 2002, 3169-3171.
Kim et al., "Octamer-based genome scanning distinguishes a unique subpopulation of *Escherichia coli* O157:H7 strains in cattle", *Proceedings of the National Science Academy*, vol. 96, No. 23, Nov. 9, 1999, 13288-13293.
Rychlik et al., "A computer program for choosing optimal oligonucleotides for filter hybridization, sequencing and in vitro amplification of DNA", *Nucleic Acids Research*, vol. 17, No. 21, Nov. 11, 1989, 8543-8551.
Unknown, "*E. coli* K12 MG1655 biochip probe SEQ ID 6481", *DATABASE Geneseq* [Online], XP002591065 retrieved from EBI Accession No. GSN:ACD75205, Sep. 18, 2003.
Unknown, "*E. coli* K12 MG1655 biochip probe SEQ ID 9813", *DATABASE Geneseq* [Online], XP002591064 retrieved from EBI Accesion No. GSN:ACD78537, Sep. 19, 2013.
Unknown, "Enterohaemorragic *E. coli* O157:H7-specific nucleic acid SEQ ID No. 1815", *DATABASE Geneseq* [Online], XP002591066 retrieved from EBI accession No. GSN:ADC01717, Dec. 4, 2003.

*Primary Examiner* — Kenneth Horlick

(57) ABSTRACT

Disclosed are methods and kits for the specific detection of *E. coli* O157:H7 and not *E. coli* O55:H7 from samples such as: complex food matrices, water, beverages, fermentation broths, forensic & biological samples, and environmental samples including food processing and manufacturing surfaces. In some embodiments, a method of the disclosure comprises: hybridizing at least a first pair of polynucleotide primers to at least a first target polynucleotide sequence, hybridizing at least a second pair of polynucleotide primers to at least a second target polynucleotide sequence, amplifying the at least first and at least second target polynucleotide sequences, and detecting the first and second amplified target polynucleotide sequence products, wherein the detection of both the first amplified target polynucleotide sequence product and the second amplified target polynucleotide sequence product is indicative of the presence of *E. coli* O157:H7 in a sample and not *E. coli* O55:H7.

17 Claims, 11 Drawing Sheets

FIGURE 1:

| Assay No. | SEQ ID No. | Primer / Probe |
|---|---|---|
| 18185 | | |
| | 1 | CTTCCTGCAACTTGCAACTTGAA |
| | 2 | CTCGCCTGATCGACAACAAAATG |
| | 3 | AGCTGGCGTAATACTTATACTCTA |
| 18874 | | |
| | 1 | CTTCCTGCAACTTGCAACTTGAA |
| | 4 | CGCCTGATCGACAACAAAATGG |
| | 3 | AGCTGGCGTAATACTTATACTCTA |
| 18935 | | |
| | 1 | CTTCCTGCAACTTGCAACTTGAA |
| | 5 | GATGCTCGCCTGATCGACA |
| | 3 | AGCTGGCGTAATACTTATACTCTA |
| 18953 | | |
| | 1 | CTTCCTGCAACTTGCAACTTGAA |
| | 6 | GCCTGATCGACAACAAAATGGT |
| | 3 | AGCTGGCGTAATACTTATACTCTA |

FIGURE 2:

Inclusion panel

| Applied Biosystems Collection # | Organism | 18158 Ct | 18874 Ct | 18953 Ct | Result |
|---|---|---|---|---|---|
| PE30 | E. coli O157:H7 | 29.67 | 29.47 | 32.01 | Positive |
| PE40 | E. coli O157:NM | 25.34 | 25.08 | 28.03 | Positive |
| PE677 | E. coli O157:H7 | 26.03 | 25.92 | 26.77 | Positive |
| PE678 | E. coli O157:H7 | 26.44 | 26.05 | 27.35 | Positive |
| PE679 | E. coli O157:H7 | 28.48 | 28.54 | 29.23 | Positive |
| PE700 | E. coli O157:H7 | 29.54 | 29.22 | 31.49 | Positive |
| PE701 | E. coli O157:H7 | 28.72 | 28.05 | 29.38 | Positive |
| PE702 | E. coli O157:H7 | 30.43 | 30.15 | 32.04 | Positive |
| PE703 | E. coli O157:H7 | 29.43 | 29.43 | 33.00 | Positive |

Exclusion panel

| | | | | | |
|---|---|---|---|---|---|
| PE006 | Salmonella typhimurium | No signal | No signal | No signal | Negative |
| PE034 | E. coli O111:NM | No signal | No signal | No signal | Negative |
| PE332 | Salmonella typhimurium LT2 | No signal | No signal | No signal | Negative |
| PE687 | E. coli O48:H21 | No signal | No signal | No signal | Negative |
| PE738 | E. coli O55:HNM | No signal | No signal | No signal | Negative |
| PE805 | E. coli O8:NM | No signal | No signal | No signal | Negative |
| PE813 | E. coli O134:NM | No signal | No signal | No signal | Negative |
| PE822 | E. coli O150:H- | No signal | No signal | No signal | Negative |
| PE830 | E. coli O159:H- | No signal | No signal | No signal | Negative |
| PE839 | E. coli O140: | No signal | No signal | No signal | Negative |
| PE704 | E. coli O55:H7 | No signal | No signal | No signal | Negative |
| PE013 | Salmonella enteritidis | No signal | No signal | No signal | Negative |
| PE036 | E. coli O145:NM | No signal | No signal | No signal | Negative |
| PE341 | Shigella | No signal | No signal | No signal | Negative |
| PE688 | E. coli O28:H35 | No signal | No signal | No signal | Negative |
| PE739 | E. coli O55:HNM | No signal | No signal | No signal | Negative |
| PE806 | E. coli O9: | No signal | No signal | No signal | Negative |
| PE814 | E. coli O135:NM | No signal | No signal | No signal | Negative |
| PE823 | E. coli O151:H1 | No signal | No signal | No signal | Negative |
| PE831 | E. coli O160:NM | No signal | No signal | No signal | Negative |
| PE840 | E. coli O142:NM | No signal | No signal | No signal | Negative |
| PE705 | E. coli O55:H7 | No signal | No signal | No signal | Negative |
| PE014 | Salmonella enteritidis | No signal | No signal | No signal | Negative |
| PE037 | E. coli O145:NM | No signal | No signal | No signal | Negative |
| PE526 | Legionella pneumophila pneumophila | No signal | No signal | No signal | Negative |
| PE026 | E. coli, not O157:H7 | No signal | No signal | No signal | Negative |
| PE798 | E. coli O1:NM | No signal | No signal | No signal | Negative |
| PE807 | E. coli O18:H7 | No signal | No signal | No signal | Negative |
| PE816 | E. coli O141:H- | No signal | No signal | No signal | Negative |

Fig. 2 Continued:

| | | | | | |
|---|---|---|---|---|---|
| PE824 | E. coli O153:H- | No signal | No signal | No signal | Negative |
| PE832 | E. coli O161:H- | No signal | No signal | No signal | Negative |
| PE841 | E. coli O147:H7 | No signal | No signal | No signal | Negative |
| PE706 | E. coli O55:H7 | No signal | No signal | No signal | Negative |
| PE015 | Salmonella typhi | No signal | No signal | No signal | Negative |
| PE038 | E. coli O78:K80:H12 | No signal | No signal | No signal | Negative |
| PE571 | Vibrio cholerae | No signal | No signal | No signal | Negative |
| PE728 | E. coli O111:H(neg) | No signal | No signal | No signal | Negative |
| PE799 | E. coli O2:H5 | No signal | No signal | No signal | Negative |
| PE808 | E. coli O18:NM | No signal | No signal | No signal | Negative |
| PE817 | E. coli O143:NM | No signal | No signal | No signal | Negative |
| PE825 | E. coli O153: | No signal | No signal | No signal | Negative |
| PE833 | E. coli O163:H8 | No signal | No signal | No signal | Negative |
| PE842 | E. coli O152:NM | No signal | No signal | No signal | Negative |
| PE707 | E. coli O55:H7 | No signal | 38.59 | No signal | Weak positive |
| PE016 | Salmonella typhimurium | No signal | No signal | No signal | Negative |
| PE039 | E. coli O103:H2 | No signal | No signal | No signal | Negative |
| PE671 | E. coli O26:H11 | No signal | No signal | No signal | Negative |
| PE731 | E. coli O26:H32 | No signal | No signal | No signal | Negative |
| PE800 | E. coli O4:H- | No signal | No signal | No signal | Negative |
| PE809 | E. coli O38:H45 | No signal | No signal | No signal | Negative |
| PE818 | E. coli O144:NM | No signal | No signal | No signal | Negative |
| PE826 | E. coli O154:H25 | No signal | No signal | No signal | Negative |
| PE834 | E. coli O163:H- | No signal | No signal | No signal | Negative |
| PE843 | E. coli O155:H24 | No signal | No signal | No signal | Negative |
| PE708 | E. coli O55:H7 | No signal | 37.88 | 38.17 | Weak positive |
| PE023 | Salmonella enteritidis | No signal | No signal | No signal | Negative |
| PE050 | Shigella dysenteriae | No signal | No signal | No signal | Negative |
| PE673 | E. coli O5:NM | No signal | No signal | No signal | Negative |
| PE735 | E. coli O55:H9 | No signal | No signal | No signal | Negative |
| PE802 | E. coli O5:H- | No signal | No signal | No signal | Negative |
| PE810 | E. coli O45:H- | No signal | No signal | No signal | Negative |
| PE819 | E. coli O145:NM | No signal | No signal | No signal | Negative |
| PE827 | E. coli O156:H8 | No signal | No signal | No signal | Negative |
| PE835 | E. coli O164:NM | No signal | No signal | No signal | Negative |
| PE340 | Shigella | No signal | No signal | No signal | Negative |
| PE732 | E. coli O55:H7 | No signal | No signal | No signal | Negative |
| PE031 | E. coli O26:H11 | No signal | No signal | No signal | Negative |
| PE060 | Listeria monocytogenes | No signal | No signal | No signal | Negative |
| PE684 | E. coli O137:H41 | No signal | No signal | No signal | Negative |
| PE736 | E. coli O55:H9 | No signal | No signal | No signal | Negative |
| PE803 | E. coli O5:H- | No signal | No signal | No signal | Negative |
| PE811 | E. coli O82:H8 | No signal | No signal | No signal | Negative |
| PE820 | E. coli O146:H21 | No signal | No signal | No signal | Negative |
| PE828 | E. coli O156: | No signal | No signal | No signal | Negative |
| PE836 | E. coli O39:H4 | No signal | No signal | No signal | Negative |
| PE733 | E. coli O55:H7 | 37.16 | 36.79 | 37.38 | Weak positive |
| PE032 | E. coli O26:H11 | No signal | No signal | No signal | Negative |

Fig. 2 Continued:

| PE331 | Salmonella typhimurium LT2 | No signal | No signal | No signal | Negative |
|---|---|---|---|---|---|
| PE685 | E. coli O26:H11 | No signal | No signal | No signal | Negative |
| PE737 | E. coli O55:HNM | No signal | No signal | No signal | Negative |
| PE804 | E. coli O6:H1 | No signal | No signal | No signal | Negative |
| PE812 | E. coli O124 | No signal | No signal | No signal | Negative |
| PE821 | E. coli O148:H28 | No signal | No signal | No signal | Negative |
| PE829 | E. coli O158: | No signal | No signal | No signal | Negative |
| PE838 | E. coli O133:NM | No signal | No signal | No signal | Negative |
| PE674 | E. coli O55:H7 | 39.01 | 39.47 | 38.01 | Weak positive |
| PE734 | E. coli O55:H7 | 39.11 | 39.18 | 38.14 | Weak positive |

FIGURE: 3

SEQ ID NO: 111

Position          315                                                                                                                    411

O157:H7   GCTTGCCGCCTTCCTGCAACTTGAATTATTTAGAGTATAAGTATTACGCCAGCTCGACCATTTGTTGTCGATCAGGCGAGCATCGCCAA

O55:H7    GCTTGCCGCCTTCCTGCAACTTG------AATTATTTAGAGTATAAGTATTACGCCAGCTCGACCATTTGTTGTCGATCAGGCGAGCATCGCCAA
                                 >------< 7 nucleotide insertion (direct repeat) in O157:H7

18158-for →                    ← 18158 probe →                          ← 18158-rev

FIGURE 4:

| Oligo | SEQ ID NO | Sequence | Gene* |
|---|---|---|---|
| 19055-for | 7 | TGACAGTATCATTACAAAGCCAAATCAGT | Z1328 |
| 19055-rev | 8 | GGCCACTACGCCCTTAATCTC | |
| 19055-probe | 9 | ACTGAATAAAGAGTTAAACGCC | |
| 19056-for | 10 | AGCAGCCATCATTGAGTATGTGAA | Z1329 |
| 19056-rev | 11 | CCGGAACTGCTCTCATTACTTGAAA | |
| 19056-probe | 12 | ATCCGCCGACGCAGTC | |
| 19057-for | 13 | TGACAGTTCTCGCTCTGCAATTT | Z1329 |
| 19057-rev | 14 | TGATGGGTTTTCATGTCGAGGAA | |
| 19057-probe | 15 | TTTTGTAGTTTTCCAGAATTC | |
| 19058-for | 16 | CGCTTTGCAGTTTCTTCAGTATTCT | Z1329 |
| 19058-rev | 17 | TGCGCGATGCGTTTACC | |
| 19058-probe | 18 | ACCGAAACAGAGTACAATC | |
| 19059-for | 19 | GACGTTGGTGAAGTGCATGTG | Z1329 |
| 19059-rev | 20 | ACTAACGGAGTTAAAGATGGAATTTAAAGA | |
| 19059-probe | 21 | CTGCAATTTCCTGGATTTC | |
| 19060-for | 22 | GGGAAATTGTCGCCGAGAATG | Z1331-Z1332 IR† |
| 19060-rev | 23 | CCTGTACAGAGTAGCTGCTTCAAG | |
| 19060-probe | 24 | TCACGCTTACAATCTC | |
| 19061-for | 25 | TCGCTCTTGTTAGTTACAGCAATTTGA | Z1332 |
| 19061-rev | 26 | CCCCGCAATTCCACATGAC | |
| 19061-probe | 27 | CCATTTCAGCCATTACCTC | |
| 19062-for | 28 | GCCCGGCGGCTTTT | Z1333 |
| 19062-rev | 29 | CGTTTCCTGAGGAAGACCAAGAA | |
| 19062-probe | 30 | CCAGCCACCTAGCAATG | |
| 19063-for | 31 | CAATGCAATGGATGCCCTGAA | Z1333 |
| 19063-rev | 32 | GCGGTAAGGCTACACCTAAAGC | |
| 19063-probe | 33 | ACCTCAACCAGTTTATCC | |
| 19064-for | 34 | CACTCAGGCTGAAATAGGTCGTT | Z1334 |
| 19064-rev | 35 | GCATAACGGAATTACCTGCTTTGG | |
| 19064-probe | 36 | CTGTTTGGCAATGGTTTAG | |
| 19065-for | 3 | AGTTTTGATATTTTACACAGGAGTAATGATGGA | Z1340 |
| 19065-rev | 38 | CCCATCCACTGAAACACCAGAATC | |
| 19065-probe | 39 | CAAAGGTTTCATGTTATTTTC | |
| 19066-for | 40 | CAGAGTGCAGCAGAGAAAGTCT | Z1341 |
| 19066-rev | 41 | GCCATCAAAGCGGAATCTGTTTT | |
| 19066-probe | 42 | CCAGAGCTCAATCATC | |
| 19067-for | 43 | CTCGGAAAGACTGGCTTCCT | Z1341 |
| 19067-rev | 44 | CCGTGCTTACGATTATACTCCTGAT | |
| 19067-probe | 45 | AACCAGCATGGATCTACT | |
| 19068-for | 46 | TGAGTTAAATATGCGTGTTTGACAATGAATG | Z1341 |
| 19068-rev | 47 | CAGTGACATAGCATATCTTAAGCATCCT | |
| 19068-probe | 48 | ACGCATGACTAAACATATGGA | |
| 19069-for | 49 | CCAATCACCAACAACCAAATTCCT | Z1341-Z1342 IR |
| 19069-rev | 50 | GCTTGATGCTATTTACCTCTGCAC | |
| 19069-probe | 51 | TTGGCGCAACTTCATG | |
| 19070-for | 52 | TGATGGTCAGCACGTAATTATTTTATGT | Z1781, Z6065 |
| 19070-rev | 53 | ATTCATCACCATTACGGACTACATCAAAA | |
| 19070-probe | 54 | CTTTATGCGCAATATCG | |
| 19071-for | 55 | TGATGGCGCATTCGTTCTTTATG | Z1781, Z6065 |
| 19071-rev | 56 | GCGGCTCTGTGTTTCGAAAA | |
| 19071-probe | 57 | ACCGTCTCGATATTGC | |

Fig. 4 Continued:

| | | | |
|---|---|---|---|
| 19072-for | 55 | TGATGGCGCATTCGTTCTTTATG | Z1781, Z6065 |
| 19072-rev | 56 | GCGGCTCTGTGTTTCGAAAA | |
| 19072-probe | 58 | TCGAGACGGTGAGTTTTT | Z1781, Z6065 |
| 19073-for | 59 | CGCAATATCGAGACGGTGAGTT | Z1781, Z6065 |
| 19073-rev | 56 | GCGGCTCTGTGTTTCGAAAA | |
| 19073-probe | 60 | CCATTACGGACTACATCAAAA | |
| 19074-for | 61 | CTTAAAATATCGCGGGCTTCGAAAT | Z1920-Z1921 IR |
| 19074-rev | 62 | TGCCGCTGAGATATCCTAAGCT | |
| 19074-probe | 63 | CTAGCCTCTGAAAATACATTTAT | |
| 19075-for | 64 | GCTGCAGTCCAGGGTACTC | Z1921 |
| 19075-rev | 65 | CCGTTCCTTAACTCAAAATGGCAAT | |
| 19075-probe | 66 | CCCAGCATTAACTAATTCAG | |
| 19076-for | 67 | CGAGAAGAGATGTGTAACACGCAAT | Z1922 |
| 19076-rev | 68 | GTTTGGACAATCCATTGGTGGAATT | |
| 19076-probe | 69 | CCACTGATCGAACCTTT | |
| 19077-for | 70 | GTTGTTTCTCAGCGCTGTATGTATC | Z1923 |
| 19077-rev | 71 | CGCAGTGAAAACTCTGGAGTGATTA | |
| 19077-probe | 72 | ATCTTCATCCACTTATTATCG | |
| 19078-for | 73 | GTATGGCGTTGTTTTTCTCAATCAGA | Z1924-Z1925 IR |
| 19078-rev | 74 | CCAAGAAACAGACTTCATTAGGAAGAGT | |
| 19078-probe | 75 | ACGGCGGTAGTTGTTAAT | |
| 19079-for | 76 | TCCCTTTTGGTGGTTCTGTTAGATC | Z3276 |
| 19079-rev | 77 | AGGAAGTAATACTATTTTGCGTGGTAAAACA | |
| 19079-probe | 78 | CAAACCCTACACCATTATC | |
| 19080-for | 79 | ACTAAGTCACTGCTAGAAAGATATACAACCA | Z3276 |
| 19080-rev | 80 | GGAAGGAACAATTACGTTGAAATGTGA | |
| 19080-probe | 81 | CCGCGATGCTTGTTTTTTGTCG | |
| 19081-for | 82 | CTGTTCGCCGCAATCTTTCC | Z3276 |
| 19081-rev | 83 | CCTGTAAGCCTGAAAACACCGTTA | |
| 19081-probe | 84 | AAGGCGATATCATCTACTTTTA | |
| 19082-for | 85 | GTAAATGTATCCCCCGCCAGT | Z3276 |
| 19082-rev | 86 | TGGTTGGGTATTTGTAAGGCATTGA | |
| 19082-probe | 87 | TTGCTGGTGAGATAATTC | |
| 19083-for | 88 | TGCAATCACGGTATCTGAAATAAACCA | Z3276 |
| 19083-rev | 89 | GCGCAGGCAGTATTACCTTATGT | |
| 19083-probe | 90 | TAGCCAGAGGCACACCTG | |

\* EDL933, GenBank Accession No. AE005174.2  † IR, intergenic region

FIGURE 5:

Inclusion panel

| Applied Biosystems Collection # | Organism | 18158, FAM Ct | 19055, VIC Ct | IPC, NED Ct | Result |
|---|---|---|---|---|---|
| PE028 | E. coli O157:H7 | 32.38 | 33.23 | 31.85 | Positive |
| PE048 | E. coli O157:H7 | 27.29 | 29.74 | 31.21 | Positive |
| PE691 | E. coli O157:H7 | 33.16 | 33.73 | 31.61 | Positive |
| PE744 | E. coli O157:H7 | 31.91 | 33.61 | 31.40 | Positive |
| PE776 | E. coli O157:H7 | 31.46 | 33.00 | 31.46 | Positive |
| PE786 | E. coli O157:H7 | 34.83 | 35.83 | 31.58 | Positive |
| PE937 | E. coli O157:H7 | 33.12 | 34.00 | 31.63 | Positive |
| PE029 | E. coli O157:H7 | 31.36 | 32.34 | 31.50 | Positive |
| PE049 | E. coli O157:H7 | 30.20 | 31.22 | 31.41 | Positive |
| PE692 | E. coli O157:H7 | 33.25 | 34.86 | 31.83 | Positive |
| PE700 | E. coli O157:H7 | 33.24 | 35.11 | 31.65 | Positive |
| PE745 | E. coli O157:H7 | 28.91 | 30.22 | 30.99 | Positive |
| PE778 | E. coli O157:H7 | 30.86 | 32.06 | 31.57 | Positive |
| PE787 | E. coli O157:H7 | 32.01 | 32.84 | 31.72 | Positive |
| PE938 | E. coli O157:H7 | 32.56 | 34.00 | 31.37 | Positive |
| PE030 | E. coli O157:H7 | 34.09 | 35.21 | 31.51 | Positive |
| PE056 | E. coli O157:H7 | 28.44 | 29.75 | 31.11 | Positive |
| PE693 | E. coli O157:H7 | 33.05 | 33.88 | 31.44 | Positive |
| PE701 | E. coli O157:H7 | 31.85 | 33.48 | 31.42 | Positive |
| PE769 | E. coli O157:H7 | 31.04 | 32.01 | 31.40 | Positive |
| PE779 | E. coli O157:H7 | 33.17 | 34.16 | 31.59 | Positive |
| PE788 | E. coli O157:H7 | 31.67 | 32.33 | 31.19 | Positive |
| PE939 | E. coli O157:H7 | 33.30 | 34.30 | 31.33 | Positive |
| PE035 | E. coli O157:H7 | 34.72 | 35.26 | 31.42 | Positive |
| PE057 | E. coli O157:H7 | 28.21 | 29.01 | 30.98 | Positive |
| PE694 | E. coli O157:H7 | 33.25 | 34.21 | 31.29 | Positive |
| PE702 | E. coli O157:H7 | 33.75 | 34.54 | 31.14 | Positive |
| PE770 | E. coli O157:H7 | 33.36 | 34.86 | 31.36 | Positive |
| PE781 | E. coli O157:H7 | 32.03 | 32.71 | 31.34 | Positive |
| PE790 | E. coli O157:H7 | 33.98 | 34.86 | 31.45 | Positive |
| PE940 | E. coli O157:H7 | 32.59 | 33.82 | 31.34 | Positive |
| PE040 | E. coli O157:H7 | 30.49 | 31.48 | 31.36 | Positive |
| PE677 | E. coli O157:H7 | 28.36 | 29.45 | 31.07 | Positive |
| PE695 | E. coli O157:H7 | 34.52 | 34.96 | 31.20 | Positive |
| PE703 | E. coli O157:H7 | 33.40 | 35.26 | 31.32 | Positive |
| PE772 | E. coli O157:H7 | 34.61 | 35.48 | 31.48 | Positive |
| PE782 | E. coli O157:H7 | 27.22 | 28.07 | 30.49 | Positive |
| PE791 | E. coli O157:H7 | 30.79 | 31.59 | 31.27 | Positive |
| PE941 | E. coli O157:H7 | 34.45 | 35.31 | 31.16 | Positive |
| PE045 | E. coli O157:H7 | 27.04 | 28.06 | 30.57 | Positive |
| PE678 | E. coli O157:H7 | 28.99 | 30.17 | 31.13 | Positive |
| PE696 | E. coli O157:H7 | 32.89 | 33.84 | 31.33 | Positive |

Fig. 5 Continued:

| PE741 | E. coli O157:H7 | 33.38 | 34.23 | 31.40 | Positive |
|---|---|---|---|---|---|
| PE773 | E. coli O157:H7 | 33.54 | 34.41 | 31.28 | Positive |
| PE783 | E. coli O157:H7 | 33.30 | 34.88 | 31.24 | Positive |
| PE792 | E. coli O157:H7 | 32.49 | 32.96 | 31.39 | Positive |
| PE942 | E. coli O157:H7 | 30.97 | 31.91 | 31.09 | Positive |
| PE046 | E. coli O157:H7 | 29.13 | 30.11 | 31.11 | Positive |
| PE679 | E. coli O157:H7 | 31.14 | 32.47 | 31.29 | Positive |
| PE697 | E. coli O157:H7 | 33.80 | 35.40 | 31.38 | Positive |
| PE742 | E. coli O157:H7 | 30.60 | 31.58 | 31.22 | Positive |
| PE774 | E. coli O157:H7 | 31.80 | 33.08 | 31.28 | Positive |
| PE784 | E. coli O157:H7 | 31.46 | 32.49 | 31.54 | Positive |
| PE795 | E. coli O157:H7 | 32.95 | 33.10 | 31.55 | Positive |
| PE943 | E. coli O157:H7 | 34.83 | 36.08 | 31.30 | Positive |
| PE047 | E. coli O157:H7 | 31.54 | 32.59 | 31.69 | Positive |
| PE690 | E. coli O157:H7 | 31.36 | 32.29 | 31.33 | Positive |
| PE698 | E. coli O157:H7 | 33.06 | 34.17 | 31.82 | Positive |
| PE743 | E. coli O157:H7 | 33.41 | 34.59 | 31.61 | Positive |
| PE775 | E. coli O157:H7 | 35.17 | 35.83 | 31.67 | Positive |
| PE785 | E. coli O157:H7 | 35.56 | 36.51 | 31.80 | Positive |

Exclusion panel

| Applied Biosystems Collection # | Organism | 18158, FAM Ct | 19055, VIC Ct | IPC, NED Ct | Result |
|---|---|---|---|---|---|
| PE006 | Salmonella typhimurium | No signal | No signal | 32.20 | Negative |
| PE034 | E. coli O111:NM | No signal | No signal | 32.21 | Negative |
| PE332 | Salmonella typhimurium LT2 | No signal | No signal | 32.06 | Negative |
| PE687 | E. coli O48:H21 | No signal | No signal | 31.88 | Negative |
| PE738 | E. coli O55:HNM | No signal | No signal | 31.98 | Negative |
| PE805 | E. coli O8:NM | No signal | No signal | 31.94 | Negative |
| PE813 | E. coli O134:NM | No signal | No signal | 31.66 | Negative |
| PE822 | E. coli O150:H- | No signal | No signal | 31.64 | Negative |
| PE830 | E. coli O159:H- | No signal | No signal | 31.83 | Negative |
| PE839 | E. coli O140: | No signal | No signal | 31.56 | Negative |
| PE704 | E. coli O55:H7 | No signal | No signal | 31.82 | Negative |
| PE013 | Salmonella enteritidis | No signal | No signal | 31.94 | Negative |
| PE036 | E. coli O145:NM | No signal | No signal | 31.67 | Negative |
| PE341 | Shigella | No signal | No signal | 32.01 | Negative |
| PE688 | E. coli O28:H35 | No signal | No signal | 31.51 | Negative |
| PE739 | E. coli O55:HNM | No signal | No signal | 31.62 | Negative |
| PE806 | E. coli O9: | No signal | No signal | 31.83 | Negative |
| PE814 | E. coli O135:NM | No signal | No signal | 31.60 | Negative |
| PE823 | E. coli O151:H1 | No signal | No signal | 31.84 | Negative |
| PE831 | E. coli O160:NM | No signal | No signal | 31.81 | Negative |
| PE840 | E. coli O142:NM | No signal | No signal | 31.69 | Negative |
| PE705 | E. coli O55:H7 | No signal | No signal | 31.70 | Negative |
| PE014 | Salmonella enteritidis | No signal | No signal | 31.58 | Negative |

Fig. 5 Continued:

| PE037 | E. coli O145:NM | No signal | No signal | 31.98 | Negative |
|---|---|---|---|---|---|
| PE526 | Legionella pneumophila pneumophila | No signal | No signal | 31.55 | Negative |
| PE026 | E. coli, not O157:H7 | No signal | No signal | 31.54 | Negative |
| PE798 | E. coli O1:NM | No signal | No signal | 31.66 | Negative |
| PE807 | E. coli O18:H7 | No signal | No signal | 31.86 | Negative |
| PE816 | E. coli O141:H- | No signal | No signal | 31.94 | Negative |
| PE824 | E. coli O153:H- | No signal | No signal | 31.50 | Negative |
| PE832 | E. coli O161:H- | No signal | No signal | 31.48 | Negative |
| PE841 | E. coli O147:H7 | No signal | No signal | 31.56 | Negative |
| PE706 | E. coli O55:H7 | No signal | No signal | 31.82 | Negative |
| PE015 | Salmonella typhi | No signal | No signal | 31.65 | Negative |
| PE038 | E. coli O78:K80:H12 | No signal | No signal | 31.67 | Negative |
| PE571 | Vibrio cholerae | No signal | No signal | 31.57 | Negative |
| PE728 | E. coli O111:H(neg) | No signal | No signal | 31.31 | Negative |
| PE799 | E. coli O2:H5 | No signal | No signal | 31.81 | Negative |
| PE808 | E. coli O18:NM | No signal | No signal | 31.54 | Negative |
| PE817 | E. coli O143:NM | No signal | No signal | 31.51 | Negative |
| PE825 | E. coli O153: | No signal | No signal | 31.68 | Negative |
| PE833 | E. coli O163:H8 | No signal | No signal | 31.62 | Negative |
| PE842 | E. coli O152:NM | No signal | No signal | 31.48 | Negative |
| PE707 | E. coli O55:H7 | No signal | No signal | 31.53 | Negative |
| PE016 | Salmonella typhimurium | No signal | No signal | 31.47 | Negative |
| PE039 | E. coli O103:H2 | No signal | 32.86 | 31.67 | Negative |
| PE671 | E. coli O26:H11 | No signal | No signal | 31.32 | Negative |
| PE731 | E. coli O26:H32 | No signal | No signal | 31.47 | Negative |
| PE800 | E. coli O4:H- | No signal | No signal | 31.42 | Negative |
| PE809 | E. coli O38:H45 | No signal | No signal | 31.56 | Negative |
| PE818 | E. coli O144:NM | No signal | No signal | 31.76 | Negative |
| PE826 | E. coli O154:H25 | No signal | No signal | 31.55 | Negative |
| PE834 | E. coli O163:H- | No signal | No signal | 31.45 | Negative |
| PE843 | E. coli O155:H24 | No signal | No signal | 31.48 | Negative |
| PE708 | E. coli O55:H7 | 39.12 | No signal | 31.60 | Negative |
| PE023 | Salmonella enteritidis | No signal | No signal | 31.33 | Negative |
| PE050 | Shigella dysenteriae | No signal | No signal | 31.46 | Negative |
| PE673 | E. coli O5:NM | No signal | No signal | 31.46 | Negative |
| PE735 | E. coli O55:H9 | No signal | No signal | 31.45 | Negative |
| PE802 | E. coli O5:H- | No signal | No signal | 31.51 | Negative |
| PE810 | E. coli O45:H- | No signal | No signal | 31.86 | Negative |
| PE819 | E. coli O145:NM | No signal | No signal | 31.92 | Negative |
| PE827 | E. coli O156:H8 | No signal | No signal | 31.69 | Negative |
| PE835 | E. coli O164:NM | No signal | No signal | No signal | Negative |
| PE340 | Shigella | No signal | No signal | 31.23 | Negative |
| PE732 | E. coli O55:H7 | No signal | No signal | 31.34 | Negative |
| PE031 | E. coli O26:H11 | No signal | 36.51 | 31.51 | Negative |
| PE060 | Listeria monocytogenes | No signal | No signal | 31.76 | Negative |
| PE684 | E. coli O137:H41 | No signal | No signal | 31.64 | Negative |
| PE736 | E. coli O55:H9 | No signal | No signal | 31.83 | Negative |
| PE803 | E. coli O5:H- | No signal | No signal | 31.69 | Negative |

Fig. 5 Continued:

| PE811 | E. coli O82:H8 | No signal | No signal | 31.99 | Negative |
|---|---|---|---|---|---|
| PE820 | E. coli O146:H21 | No signal | No signal | 31.77 | Negative |
| PE828 | E. coli O156: | No signal | No signal | 31.77 | Negative |
| PE836 | E. coli O39:H4 | No signal | No signal | 31.59 | Negative |
| PE733 | E. coli O55:H7 | 38.69 | No signal | 31.60 | Negative |
| PE032 | E. coli O26:H11 | No signal | No signal | 31.75 | Negative |
| PE331 | Salmonella typhimurium LT2 | No signal | No signal | 31.51 | Negative |
| PE685 | E. coli O26:H11 | No signal | No signal | 31.55 | Negative |
| PE737 | E. coli O55:HNM | No signal | No signal | 31.94 | Negative |
| PE804 | E. coli O6:H1 | No signal | No signal | 31.91 | Negative |
| PE812 | E. coli O124 | No signal | No signal | 32.02 | Negative |
| PE821 | E. coli O148:H28 | No signal | No signal | 31.84 | Negative |
| PE829 | E. coli O158: | No signal | No signal | 32.06 | Negative |
| PE838 | E. coli O133:NM | No signal | No signal | 31.69 | Negative |
| PE674 | E. coli O55:H7 | No signal | No signal | 31.49 | Negative |
| PE734 | E. coli O55:H7 | No signal | No signal | 31.77 | Negative |

SEQUENCE LISTING

```
<160> NUMBER OF SEQ ID NOS: 111

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
cttcctgcaa cttgcaactt gaa                                            23

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ctcgcctgat cgacaacaaa atg                                            23

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3
agctggcgta atacttatac tcta                                           24
```

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cgcctgatcg acaacaaaat gg                                              22

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gatgctcgcc tgatcgaca                                                  19

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gcctgatcga acaacaaatg gt                                              22

<210> SEQ ID NO 7
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tgacagtatc attacaaagc caaatcagt                                       29

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ggccactacg cccttaatct c                                               21

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 9
actgaataaa gagttaaacg cc                                              22

```
<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
agcagccatc attgagtatg tgaa                                           24

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ccggaactgc tctcattact tgaaa                                          25

<210> SEQ ID NO 12
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 12
atccgccgac gcagtc                                                    16

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
tgacagttct cgctctgcaa ttt                                            23

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
tgatgggttt tcatgtcgag gaa                                            23

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 15
ttttgtagtt ttccagaatt c                                              21

<210> SEQ ID NO 16
```

```
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
cgctttgcag tttcttcagt attct                                          25

<210> SEQ ID NO 17
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
tgcgcgatgc gtttacc                                                   17

<210> SEQ ID NO 18
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 18
accgaaacag agtacaatc                                                 19

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gacgttggtg aagtgcatgt g                                              21

<210> SEQ ID NO 20
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
actaacggag ttaaagatgg aatttaaaga                                     30

<210> SEQ ID NO 21
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 21
ctgcaatttc ctggatttc                                                 19

<210> SEQ ID NO 22
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gggaaattgt cgccgagaat g                                              21

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
cctgtacaga gtagctgctt caag                                           24

<210> SEQ ID NO 24
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 24
tcacgcttac aatctc                                                    16

<210> SEQ ID NO 25
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
tcgctcttgt tagttacagc aatttga                                        27

<210> SEQ ID NO 26
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
ccccgcaatt ccacatgac                                                 19

<210> SEQ ID NO 27
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 27
ccatttcagc cattacctc                                                 19

<210> SEQ ID NO 28
<211> LENGTH: 14
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 28
gcccggcggc tttt                                                    14

<210> SEQ ID NO 29
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
cgtttcctga ggaagaccaa gaa                                          23

<210> SEQ ID NO 30
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 30
ccagccacct agcaatg                                                 17

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
caatgcaatg gatgccctga a                                            21

<210> SEQ ID NO 32
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
gcggtaaggc tacacctaaa gc                                           22

<210> SEQ ID NO 33
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 33
acctcaacca gtttatcc                                                18

<210> SEQ ID NO 34
<211> LENGTH: 23
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 34
cactcaggct gaaataggtc gtt                                              23

<210> SEQ ID NO 35
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
gcataacgga attacctgct ttgg                                             24

<210> SEQ ID NO 36
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 36
ctgtttggca atggtttag                                                   19

<210> SEQ ID NO 37
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
agttttgata ttttacacag gagtaatgat gga                                   33

<210> SEQ ID NO 38
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
cccatccact gaaacaccag aatc                                             24

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 39
caaaggtttc atgttatttt c                                                21

<210> SEQ ID NO 40
<211> LENGTH: 22
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 40
cagagtgcag cagagaaagt ct                                                 22

<210> SEQ ID NO 41
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
gccatcaaag cggaatctgt ttt                                                23

<210> SEQ ID NO 42
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 42
ccagagctca atcatc                                                        16

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
ctcggaaaga ctggcttcct                                                    20

<210> SEQ ID NO 44
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
ccgtgcttac gattatactc ctgat                                              25

<210> SEQ ID NO 45
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 45
aaccagcatg gatctact                                                      18

<210> SEQ ID NO 46
<211> LENGTH: 31
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 46
tgagttaaat atgcgtgttt gacaatgaat g                                  31

<210> SEQ ID NO 47
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
cagtgacata gcatatctta agcatcct                                      28

<210> SEQ ID NO 48
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 48
acgcatgact aaacatatgg a                                             21

<210> SEQ ID NO 49
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
ccaatcacca acaaccaaat tcct                                          24

<210> SEQ ID NO 50
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
gcttgatgct atttacctct gcac                                          24

<210> SEQ ID NO 51
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 51
ttggcgcaac ttcatg                                                   16

<210> SEQ ID NO 52
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 52
tgatggtcag cacgtaatta ttttatgt                                          28

<210> SEQ ID NO 53
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
attcatcacc attacggact acatcaaaa                                         29

<210> SEQ ID NO 54
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 54
ctttatgcgc aatatcg                                                      17

<210> SEQ ID NO 55
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
tgatggcgca ttcgttcttt atg                                               23

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
gcggctctgt gtttcgaaaa                                                   20

<210> SEQ ID NO 57
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 57
accgtctcga tattgc                                                       16

<210> SEQ ID NO 58
<211> LENGTH: 18
<212> TYPE: DNA
<213> ORGANISM: Artificial Sequence
<220> FEATURE:
<223> OTHER INFORMATION: Description of Artificial Sequence: Synthetic
      probe
```

```
<400> SEQUENCE: 58
tcgagacggt gagttttt                                                18

<210> SEQ ID NO 59
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
cgcaatatcg agacggtgag tt                                           22

<210> SEQ ID NO 60
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 60
ccattacgga ctacatcaaa a                                            21

<210> SEQ ID NO 61
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
cttaaaatat cgcgggcttc gaaat                                        25

<210> SEQ ID NO 62
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
tgccgctgag atatcctaag ct                                           22

<210> SEQ ID NO 63
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 63
ctagcctctg aaaatacatt tat                                          23

<210> SEQ ID NO 64
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
```
gctgcagtcc agggtactc                                          19

<210> SEQ ID NO 65
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
ccgttcctta actcaaaatg gcaat                                   25

<210> SEQ ID NO 66
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 66
cccagcatta actaattcag                                         20

<210> SEQ ID NO 67
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
cgagaagaga tgtgtaacac gcaat                                   25

<210> SEQ ID NO 68
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
gtttggacaa tccattggtg gaatt                                   25

<210> SEQ ID NO 69
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 69
ccactgatcg aacctttt                                           17

<210> SEQ ID NO 70
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70

```
gttgtttctc agcgctgtat gtatc                                       25
```

<210> SEQ ID NO 71
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71

```
cgcagtgaaa actctggagt gatta                                       25
```

<210> SEQ ID NO 72
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 72

```
atcttcatcc acttattatc g                                           21
```

<210> SEQ ID NO 73
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73

```
gtatggcgtt gttttctca atcaga                                       26
```

<210> SEQ ID NO 74
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74

```
ccaagaaaca gacttcatta ggaagagt                                    28
```

<210> SEQ ID NO 75
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 75

```
acggcggtag ttgttaat                                               18
```

<210> SEQ ID NO 76
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76

```
tcccttttgg tggttctgtt agatc                                       25
```

<210> SEQ ID NO 77
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
aggaagtaat actattttgc gtggtaaaac a                                31

<210> SEQ ID NO 78
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 78
caaaccctac accattatc                                              19

<210> SEQ ID NO 79
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
actaagtcac tgctagaaag atatacaacc a                                31

<210> SEQ ID NO 80
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
ggaaggaaca attacgttga aatgtga                                     27

<210> SEQ ID NO 81
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 81
ccgcgatgct tgttttttgt cg                                          22

<210> SEQ ID NO 82
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
ctgttcgccg caatctttcc                                             20

<210> SEQ ID NO 83
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
cctgtaagcc tgaaaacacc gtta                                          24

<210> SEQ ID NO 84
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 84
aaggcgatat catctacttt ta                                            22

<210> SEQ ID NO 85
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
gtaaatgtat cccccgccag t                                             21

<210> SEQ ID NO 86
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
tggttgggta tttgtaaggc attga                                         25

<210> SEQ ID NO 87
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 87
ttgctggtga gataattc                                                 18

<210> SEQ ID NO 88
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
tgcaatcacg gtatctgaaa taaacca                                       27

```
<210> SEQ ID NO 89
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
gcgcaggcag tattacctta tgt                                            23

<210> SEQ ID NO 90
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 90
tagccagagg cacacctg                                                  18

<210> SEQ ID NO 91
<211> LENGTH: 560
<212> TYPE: DNA
<213> ORGANISM: Escherichia coli

<400> SEQUENCE: 91
cttttgccag tggtaatgga tggatgaaat tacccaacgg gaaaatcctg caatatggtc    60
gtggtgcggt tacgccgaca ttatcgacgc aaacaatgag aattacattc agcatccctt   120
tccccaaaaa agcggactgc gccatgctta ctcattctgg tgatggcggt gcgcctttag   180
gcgctgggcg agggttcgtg atgactgcag aaggcccaac gttaaccggc tttaattctg   240
cttacagaac gtcatcaacc agcgacacgg tatcgatgaa ttacagttgg tgggctgttg   300
gtgagtaatt ttattcaggg tgatttatat ggacgaatat gtttatagcg caaggcataa   360
tgcttttttc cctgtggata tgattgataa atataaatca gagggatggg atttatcaga   420
cgctaaggaa gtaaatcaaa atattatcag tgagtttatg gctgaaccgc cacaaggaaa   480
aatccgtatt gccggagatg atgggctgcc tgcgtgggca gatattcctc cacccacgca   540
tgaagagctt attgaaatta                                               560

<210> SEQ ID NO 92
<211> LENGTH: 601
<212> TYPE: DNA
<213> ORGANISM: Escherichia coli

<400> SEQUENCE: 92
ccatgccctg cctgtaacgc tctttctggc tttttagaga agggcggtta ttacattttt    60
aactgtccag aacatgttga atttcatata tcaaaacttg acagtatcat tacaaagcca   120
aatcagtatc agtctgattt actgaataaa gagttaaacg ccgcccgaga ttaagggcgt   180
agtggcccat taaaaatatt gcaaagacca actattgttg aactggatta aaccagtaat   240
tctctattgc tcttattgtt accatcggat gattgccggg ggttatttta agttcgggag   300
gaaaaggctc tccatcagca gccatcattg agtatgtgaa atccgccgac gcagtccctt   360
tcatgataat tccgaatttt tcaagtaatg agagcagttc cggtaatcct gtgtcatctg   420
aataactttc ctcatagaaa gaagcgattg ccgcaggaga tgcagttct cgctctgcaa    480 ttttttttgta gttttccaga attctttttt tgaatacttt tcctcgacat gaaacccat   540
```

```
caccgaggca atccgctttg cagtttcttc agtattctgg ttgtttgtta ccgaaacaga      600
g                                                                     601
```

```
<210> SEQ ID NO 93
<211> LENGTH: 123
<212> TYPE: DNA
<213> ORGANISM: Escherichia coli

<400> SEQUENCE: 93
gtaatctaca ataaaaaact gttttttgtgt caacagtttt taattgttgt tttgggcaaa      60
aaaatccctc gaaagaggga gtatgaaaat tgttcaactc agatagagaa gggaaattgt     120
cgc                                                                   123
```

```
<210> SEQ ID NO 94
<211> LENGTH: 693
<212> TYPE: DNA
<213> ORGANISM: Escherichia coli

<400> SEQUENCE: 94
ggctgtaccc atggcataac tcctcttctt gtactgtggt cacgcccggc ggcttttttg      60
tgccgccagc cacctagcaa tggtttcttc cattgatttt ttcttgtctt tgatttcttg    120
aagcattttt tcttggtctt cctcaggaaa cgcactaaaa gcttggagca gttcgcgttg    180
gcgaggacca attttcatcg tgtcaggggt gaaaatttgc tcacactctt caggaggcaa    240
taaaaaccaa tgcaatggat gccctgaaac ctcaaccagt ttatccaaac ttgaggcttt    300
aggtgtagcc ttaccgctga cccattgttg aacagttttg tgtgtcacac caattctacg    360
ggcaagctca gcctggctcc atccagtttc ctgaagaagc ttgctgattc tgtacataga    420
tacttctagg gcgctcatca ttattcaatt ttacaggtaa atactgttaa aagcatcaca    480
ataaaaaact gttgattgca tacagttttt tattgtaggc tttgcttata gttttttagag    540 gagggcaaaa tgctagatag cactcgcgaa aaaattaggc agaaatacac tcaggctgaa    600
ataggtcgtt atatggggggt cgctcaacag actgtttggc aatggtttag ctttggcgtt    660
cccccaaagc aggtaattcc gttatgccaa cta                                  693
```

```
<210> SEQ ID NO 95
<211> LENGTH: 679
<212> TYPE: DNA
<213> ORGANISM: Escherichia coli

<400> SEQUENCE: 95
cactctggct gtgcattaat tgggtaataa atatgagtaa tgacaaaaaa ttgacactga      60
gcgtttacga aaacagtccg cacatctggc gtggcggttt atctgatgtg gagctggcag    120
agtggttgat acataaagct aatgcgctgc tctggcgttt gtcagccaga gaacagcgca    180
aggaaaccag aataaagctg gctgatgcag aagcgtgtgc cgggcttatt gaggattata    240
caaatcttgg tatttcttca gcagagagtg atcccattca gcctctgagc agggagtcaa    300
tccagcacgc tggttgtatg gcacatcttg taactgctcg tcaacatgag gtgggtattg    360
gatcacttcc ggcgggatat tcgctgattc cagagctggt tgaagcaaga aaatcagttc    420
agaaaaagag agatgacgca cttcaattat tgagagagca ctatggcgcg ataccagaat    480
gcgaacagcg tcgataccct gaaggttatg aatggatgca gtctcttttt gaagttcgct    540
aatcaatatg tcgagacgaa ggtatgtttc ggcgcgcagc caggctctgt aatccgggag    600
catttcgggg ctgttacacc agcggtttgt tgctgcaaca tttaatacat gagcctgata    660
```

-continued

| aaggctttc aaaaaatac | | | 679 |

<210> SEQ ID NO 96
<211> LENGTH: 524
<212> TYPE: DNA
<213> ORGANISM: Escherichia coli
<400> SEQUENCE: 96

| agccatgcgt gattacgcaa aagtttctcc gcgattctgg ctgggagaaa cggggagaga | 60 |
| acttagaaag gcgggtgcag aagcgcaagt tgttgctttt tacctgatga catcccctca | 120 |
| cgcaaatatg ctgggtttgt attacctgcc agttttatac cttgctcatg aaaccgggct | 180 |
| tggtctggaa ggggcttcaa agggcttaa aagggctgtt gaagctggtt tttgtagcta | 240 |
| tgaccatgat gcagagatgg tctgggtcca tgaaatggca gcctggcagg ttggggaaac | 300 |
| gttgaagcct ggcgataacc gttgtgcagg tgtcaggaat gagtatgcat cattacctga | 360 |
| aaacgctttt ctgtcagtgt tttacgacag atataaaacg gatttccatc tggatgtgag | 420 |
| gcggaataat agccgaaatt cggtaagggg cttcgaaggg gcttttaagg ggcttcgaag | 480 |
| ccaagaacag gaacaggagc aggagaaaga acaggaacag gaca | 524 |

<210> SEQ ID NO 97
<211> LENGTH: 1396
<212> TYPE: DNA
<213> ORGANISM: Escherichia coli
<400> SEQUENCE: 97

| caggagtaat gatggaatag tgaaaataac atgaaacctt tggattctgg tgtttcagtg | 60 |
| gatgggaaaa gagcagatac atagaaaatg aatagcaata attcacagtc tggatgttgt | 120 |
| ttgtatgctt ataaaatgat cctagtatgc attgccggag ttgaatcagc tccaatgaag | 180 |
| aaactgagag gagtatttag aagatagcta aatggatgta attattagta tctaaaaaat | 240 |
| agtatttttg aaatgggtct aagaacacaa caatgtacaa atgagaagtt atcttttaat | 300 |
| atgttcaaag acccattagg attgatatca gttatgttag ctagattgat aaagtgatta | 360 |
| catattttct gttatatgct gaaatgaata atgctattcc agagtgcagc agagaaagtc | 420 |
| tcctgatgat tgagctctgg aaattgtaca atagaaaaat tactgtatttt ttctgtcaaa | 480 |
| atatttctca aaacagattc cgctttgatg gcttcaggat ataagatgc ggagtaatca | 540 |
| aggctaagat ttccgttaag caagcatata cttttagtgt gctttgattc tgatatatca | 600 |
| tctttaatta tcttgatgat tctttcattc tgccatagaa gtgatggtgc agatatataa | 660 |
| taatagttaa agcatgaatt atttttaag caatcaagca caaaaatagc acctagcgag | 720 |
| tgtccccata taccgattct ggaactgttc ggagcaatag tactaaccca tggcatgatc | 780 |
| tgagttagta ataattctcg gaaagactgg cttcctccac cagtaaagta gatccatgct | 840 |
| ggtttagagt tatcaacaat agcattttca ccatcaggag tataatcgta agcacggcga | 900 |
| tgaatgctaa ggttattcca agattcataa ccaagtgtaa ctaacactgg tggattgggt | 960 |
| agtgcatcaa taacaggcag aatatcagaa atgtaattgt tggcactatt cccatcaagt | 1020 |
| atataaagag ttgcattatt tttttaatg ttttttggag taaaaataca tatttttat | 1080 |
| ttggtgtcat ggttaattga gttaaatatg cgtgtttgac aatgaatgtc catatgttta | 1140 |
| gtcatgcgtt ctccccatga gcattaaagg atgcttaaga tatgctatgt cactgataaa | 1200 |
| aaatttgttg tgtgtgttta gttattttat ctacctccat tatgatttaa gactgatata | 1260 |

```
tgttatcagc aaaggtacat cgttattatt ttacctgtca atacatttga tattgattat    1320
cgtttacatc gcttgcttag gaaattgaag gcaggtaact atcatgtcaa tgaactaacc    1380
cacagtctaa cgtact                                                    1396

<210> SEQ ID NO 98
<211> LENGTH: 130
<212> TYPE: DNA
<213> ORGANISM: Escherichia coli

<400> SEQUENCE: 98
gatggtcagc acgtaattat tttatgtgat ggcgcattcg ttctttatgc gcaatatcga     60
gacggtgagt tttttgatgt agtccgtaat ggtgatgaat ttttcgaaac acagagccgc    120
aatgtaaccg                                                           130

<210> SEQ ID NO 99
<211> LENGTH: 284
<212> TYPE: DNA
<213> ORGANISM: Escherichia coli

<400> SEQUENCE: 99
tatgatatta actatcgagc aagaatatcc ccaggcactc aacagggcgc aggtcaacgt     60
gaatcggtca tgacacgaca ccgatttttgc ggaatcaatg ttgcttatga atacaacatc   120
ccgcttagta catgttcaac acatcagcaa attttgaact gggtgtggca cttaactgaa   180
aaaacatgga tgacacaaaa tgttactcgt cgcttcattg aagtagcttg tggatatcac   240
aagctagact atcgccaatg atattcaatt tttgattttt tagt                    284

<210> SEQ ID NO 100
<211> LENGTH: 1112
<212> TYPE: DNA
<213> ORGANISM: Escherichia coli

<400> SEQUENCE: 100
aagtttaaaa taaaagcccg cttaaaatat cgcgggcttc gaaatataaa tgtattttca     60
gaggctagag cttaggatat ctcagcggca attaacttat gagggatagc taaataccag   120
aagataatta gttttactta tttatctttg tttgtggttc tccttcagca agctcagcgc   180
cagtgacagg attgatgtct tcatgggatt tcaaccttgt tgccatagct tttatcatag   240
cttcttgctt ggtcgaaaga tttatcgagg ccttcccatc cccaccgtca accgctgaaa   300
ctggatcgga acatagtca aagttttcat cactgttcca actacctctg acgtcttcac    360
cttctgacat gttgtaatat acgttttgt atttctcaag tggtggtaat tttcctggtg   420
gaaaggtgtt acgaattgaa tgtaatgctt tttcaaatga agcatgtgt gctgcttccc    480 gggtcattaa aaatgccaga gtgtcttta ctccaggatc atcagtaaca ttaatgagac    540
gttcgtaaat gatctttgcc cgagcttcag ctgcaatatt tgaacgaaga tcggccgtga   600
cttcgccaat agtatcaaca taagctgcag tccagggtac tccagctgaa ttagttaatg   660
ctgggcctcc tccgtagagg agagaagtta tatggctatc attgccattt tgagttaagg   720
aacggtaaag ctcagcttca ttctcagttc cttcagcaag tgctcctttt gcacctttgt   780
tgagcatacc aacaagagaa ccaataattt cgagatgact tagttcttct gttgctatgt   840
ccatcagcat atcccttcgg cctgcatctt catcacttaa gccttgagtg aagtatcggc   900
atgctgctgc aagctcaccc tgtggcccac cgaattgttc taagagtaga ttagccaagc   960
ctgggtttgg ctcacttaca cgtactgtat attgaagttt tttcacgtgt ctaaacataa   1020
```
tgcctcctca aaagaattat tttttggctt caactccatc aatttcagat ctgaccatga    1080
attgctcagt ggtgtcagga atatggttaa ga    1112

<210> SEQ ID NO 101
<211> LENGTH: 829
<212> TYPE: DNA
<213> ORGANISM: Escherichia coli

<400> SEQUENCE: 101
tatgctttca agctgtgaaa gctggttctt tgtttcgcta atgtgctgct caattctgga      60
acgtaactca ggatagtttt ctatccggct ggccatagac tcaagcattt tttcagcttg     120
tttttccatc gcatgtgcat cacgaagcca gtcatggtaa tgttcaattc tattcataat     180
ctgtttatcc taaagaaat tgaagtctat agttcaggag ttatcctgag cttttttatt      240
aacgttatta atgccaggt ctgttaattt gacatcagta gcttttcct cttccagtgt       300 ttctttcagg agtttagccg ctttttttata tcctaattgc tcagcgagtg ttaccaaagt    360
gccataactg gcaatttcat agtgctctac ttttttgtgct gcagcaatca atgcagcatc    420
acgtacttca tttttatcag tgctttcaat tacctcattc gcctcttcga taagtccttc     480
cattgcggca cacttaattc ttttcaattt aagaccatct tcagaatcaa caacctgatc    540
gatgcgttca atttgaccat gtgtctcatc aagatgtgac tgaaaagcag cggttaattt    600
atcactatat gcagagcgac taagtttaga cagtgccttt gttagttgtt tctcagcgct    660
gtatgtatcc gataataagt ggatgaagat atcttcaaca gatttaattt gcataatcac    720
tccagagttt tcactgcgag cccgtaggct cgcagttagc ttcagttatt cacgaatgta    780
gggggtgata aattaagagt cagatttacg gccgccacca tggctattc                 829

<210> SEQ ID NO 102
<211> LENGTH: 438
<212> TYPE: DNA
<213> ORGANISM: Escherichia coli

<400> SEQUENCE: 102
tctgattttc aaattgtaaa taacatgtgc cttgtcagca cccaattaac tctagtaaca      60
aataagaaag tgtcaaataa gagattggta tgcgcatctt aatgtgagaa atagcaattg     120
taaaaatgtg tactcagtga gtataatctg ttgatatctt ggtgattaac ggaaagttta     180
ggttgtaact caaaagatta ataaatctaa atttacattt ctatatcttt tgatgtgtat     240
ggcgttgttt ttctcaatca gaacattcta aaaataatt taattacacg gcggtagttg      300
ttaatgtttt tacgactctt cctaatgaag tctgtttctt ggataaatag agaaattta      360 tcttaaggac taattacaaa aacatctata tagccacagg aatcattatt gtacttaact    420
acaatatttg agagtaaa                                                   438

<210> SEQ ID NO 103
<211> LENGTH: 122
<212> TYPE: DNA
<213> ORGANISM: Escherichia coli

<400> SEQUENCE: 103
tggctaatgt gtttcgtatc gcgctggcat cactggaagc agagccgata gcaatggtag      60
tgcctgatga aatggatttg cttacctgcc atctcgacgg tgtaactaaa acatatgctg     120
at                                                                   122

<210> SEQ ID NO 104
<211> LENGTH: 130
<212> TYPE: DNA
<213> ORGANISM: Escherichia coli

<400> SEQUENCE: 104
cggttacatt gcggctctgt gtttcgaaaa attcatcacc attacggact acatcaaaaa    60
actcaccgtc tcgatattgc gcataaagaa cgaatgcgcc atcacataaa ataattacgt   120
gctgaccatc                                                         130

<210> SEQ ID NO 105
<211> LENGTH: 272
<212> TYPE: DNA
<213> ORGANISM: Escherichia coli

<400> SEQUENCE: 105
tgtctggcgg ggcagcatat agcggcacgt atatttccgg ttccttatca gcaccgggtt    60
gctcttccag tgagaatgtc tttccggtaa atcgattcat ataaagcacg ggctctgctt   120
ccagcgaagc ctgagcaaca agggccagtg ctaaatccaa ctcaattgcc tcgagagaat   180
ttttgaatgc tgtctgtttt actgcaaatt tcatcgcctt tacatttta ctaacatgac   240 tgattaactg ctcttttgta aaagtggtca tc                                272

<210> SEQ ID NO 106
<211> LENGTH: 251
<212> TYPE: DNA
<213> ORGANISM: Escherichia coli

<400> SEQUENCE: 106
atatattttt aatgctaata gttttgataa gcattaaaat ttatgcacgc taccgcccct    60
ggcttaatcg ctaccagtgt acgaaatgat aatccatgtt aaaaaaatca tctccaagcg   120
tttattatct tattattcag agggagaaac aagactacca acaaaaaat acatatctgc   180 acactattta ttcattggta gcatagttaa ttataaaagc tcaacagcag tgatatttat   240
tgatctatag t                                                       251

<210> SEQ ID NO 107
<211> LENGTH: 970
<212> TYPE: DNA
<213> ORGANISM: Escherichia coli

<400> SEQUENCE: 107
atgactggta tattaataat gttgctattt aatgaaactc tggtttatc tgttttccat     60 aatgatgtcg ccgcgccctg atcgccgttg gccgaaattt taatggcagc tcagtccct   120 tttggtggtt ctgttagatc caacacaaac cctacaccat tatctgtttt accacgcaaa   180
atagtattac ttcctttaac taagtcactg ctagaaaagat atacaaccat attccgcgat   240
gcttgttttt tgtcgccgaa aagattatca catttcaacg taattgttcc ttccttactg   300
ttcgccgcaa tctttccctg atttctgagc tggaacaagg cgatatcatc tacttttata   360
acggtgtttt caggcttaca ggtcgtattt ttaggataat aggaaatatt taacccaagc   420
gtaaatgtat cccccgccag tttgctggtg agataattca cacaccagtt aaacttcaat   480
gccttacaaa tacccaacca aaaatcgatg gatgacgatg actcaccgcc aatatttgca   540
atcacggtat ctgaaataaa ccaggtagat tttctttctc cagtaaaatc aggtgtgcct   600
ctggctattt taaccacata aggtaatact gcctgcgcat tgctggattt cccaattgtg   660

```
tcgctggttt tacctaaaga ctctatttta acctttaatt tttcgccatt accaaaaggc    720
ccaacttcaa cccaatcact ttggatattt tttataaacta ttttatccgt gctcgtatca    780
```

```
tcgctggttt tacctaaaga ctctatttta acctttaatt tttcgccatt accaaaaggc    720
ccaacttcaa cccaatcact ttggatattt ttataaacta ttttatccgt gctcgtatca    780
caagatatcc cagtaaacac gacactttta ctaaaggaag tttcattcgc taaaatctcc    840
ccaacattaa taccatctgt aatatttaat gatgcagtag tacgcaccc agcccaggta     900 aaattagccc acaatataaa tattagtaat attctatttc tgaacatcat atttcacctc    960
tcaccgacag                                                           970
```

<210> SEQ ID NO 108
<211> LENGTH: 103
<212> TYPE: DNA
<213> ORGANISM: Escherichia coli

<400> SEQUENCE: 108

```
acatgcccgc gagaaaatca acatagttgc tgaaaaccgt gggctgacta tggctgaact    60
ggaagaccgc ctggctccag atttagggct tgatagcagt ggc                     103
```

<210> SEQ ID NO 109
<211> LENGTH: 205
<212> TYPE: DNA
<213> ORGANISM: Escherichia coli

<400> SEQUENCE: 109

```
tgtagtgtgc gatgcaaacg gcaaagtcct gaaagattta cctaagccaa accagagcga    60
tgaaaaaact caggcaactg acgcggttaa tctcttcaaa cagttgaaaa aagatgtacg   120
cgccatagcc agccagcaga ttgatcgtct ggaacaggct atgtgccagc gcagacgctg   180
gacggcagag cagttccgcc tgttt                                         205
```

<210> SEQ ID NO 110
<211> LENGTH: 483
<212> TYPE: DNA
<213> ORGANISM: Escherichia coli

<400> SEQUENCE: 110

```
caatgcgccg aatgggagcg aaaagcatta agcaactttg aagagtgtgc tgcgatggct    60
gaacgtatcg aagagatgca gacaaaatct gcaccagatt cgtttggcat catcggtgaa   120
aatattcgaa cacaggacaa tcgaataacg tcagatccca tgttttgtgt gtatcaaaag   180
cgcgaaatcg ctgttgatgc tgattatgac catgaccgga ttgtctgggt tgacgaagat   240
ggcaatgaag ccaataaacg ccatagtcgt cgtctcgagc tacttcatga aaactttcga   300
gagccaccag aaaaatggcg gcgcgttgct gtgaaagata ttgatgaatt cgttacctgc   360
tgtttcaccg aacaggggttg taaagactac ctggcagtca atggtcacaa tcttcgcttg   420
ccatttatat atgtaaaaag cggtttcagg aacgctgaat atatcggcat aagaaactgg   480
ctt                                                                 483
```

<210> SEQ ID NO 111
<211> LENGTH: 467
<212> TYPE: DNA
<213> ORGANISM: Escherichia coli

<400> SEQUENCE: 111

```
gtctcgggag acgttgcaga gatgacaaat ttatctcttg ctgagattga taggctgatt    60
aactaagttg tctgcgttat gaataattgc ttacagacgc catcgccatg acgtggggca   120
```

-continued

```
aattaataat tggcgccatc agccgtagcg ccagttatac tcgtcatact tcaaattgca    180
tgtgctgcgt ctgcgttcgc taaccccagt cacttactta tgtaagctcc tggggattaa    240
tgagagacat ccatgtctct caccgaaggc cagcctgcgg ctgggcaaat tcgttcctga    300
cgaatttgtc actcgcttgc cgccttcctg caacttgcaa cttgaattat ttagagtata    360
agtattacgc cagctcgacc attttgttgt cgatcaggcg agcatcgcca agccaggcgg    420
ctaccagaat tactgcccgt ttgctggttt cagagaggtc atagctg                  467
```

US 8,906,628 B2

NUCLEIC ACID AMPLIFICATION METHODS FOR SPECIFIC DETECTION OF E. COLI O157:H7 WITHOUT CO-DETECTION OF E. COLI O55:H7

CROSS-REFERENCE TO RELATED APPLICATIONS

This application is a continuation of U.S. application Ser. No. 12/780,707, filed May 14, 2010, now U.S. Pat. No. 8,445,209, which claims the benefit under 35 U.S.C. §119(e) of U.S. Provisional Application No. 61/178,931 filed May 15, 2009, the contents of which are incorporated herein by reference.

FIELD OF THE INVENTION

The present teachings relate to assays and methods for the specific detection and differentiation of pathogenic organisms.

BACKGROUND

Identification of bacterial contamination in food often occurs subsequent to an outbreak of a foodborne illness. The bacterium *Escherichia coli* is frequently identified as the food contaminant of many foodborne illnesses. The serotype known as *E. coli* O157:H7 causes enterohemorrhagic colitis and possibly kidney failure. It often results in hospitalization of the infected patient and can be particularly lethal in young children and the elderly. O157:H7 is most often associated with outbreaks of foodborne illness in the United States and elsewhere in the world.

Detection of pathogenic *E. coli*, particularly serotypes causative of hemorrhagic colitis has become a public health priority. O157:H7 is frequently isolated from cattle, including healthy animals and has also been associated with illness in contaminated produce. The presence of O157:H7 in a food product released to consumers is considered as evidence of adulteration of the product. Regulations by the United States government require meat processors to screen for the presence of O157:H7 in their finished products and more stringent guidelines are being considered in a number of states for the identification of O157:H7 in other commodities and food stuffs. An assay for the rapid, sensitive and specific detection of infectious pathogens is extremely important from both a public health and economic perspective.

Many strains of genetically similar *E. coli* exist that vary dramatically in their pathogenicity. Genomic comparisons are revealing the consequences of genetic changes often underlie the emergence of new pathogenic bacteria. *E. coli* O157:H7 has been determined to have evolved stepwise from the O55:H7 which is associated with infantile diarrhea. These two serotypes are more closely related at the nucleotide level while divergence was markedly different at the gene level. Likewise, other pathogenic serotypes have been shown to be less divergent at the nucleotide level making identification of pathogenic strains difficult.

An assay utilizing molecular methods such as sequence specific amplification and detection offer significant improvements in speed, sensitivity and specificity over traditional microbiological methods. Design and development of a molecular detection assay that requires the identification of a target sequence that is present in all organisms to be detected and absent or divergent in organisms not to be detected is an unmet need for the definitive detection of the O157:H7 serotype of *E. coli*.

SUMMARY

In accordance with the embodiments, there is disclosed a method of detecting the presence of *E. coli* O157:H7 in a sample, comprising: detecting the presence of SEQ ID NO:111 or complement thereof; and detecting the presence of a sequence selected from SEQ ID NO:90-110 and complements thereof; wherein detection of SEQ ID NO:111 and detection of a sequence selected from SEQ ID NO:90-110 confirms the presence of *E. coli* O157:H7 in a sample and not *E. coli* O55:H7. The detection is by a nucleic acid amplification reaction, the amplification reaction is an end-point determination, the amplification reaction is quantitative, the quantification is a real-time PCR, the real-time PCR is a SYBR® Green Assay or the real-time PCR is a TaqMan® Assay.

In another embodiment, disclosed is an assay for the detection of *E. coli* O157:H7 in a sample comprising a) hybridizing a first pair of PCR primers selected from the group consisting of: SEQ ID NO:1-2, SEQ ID NO:1 and SEQ ID NO:4, SEQ ID NO:1 and SEQ ID NO:5, and SEQ ID NO:1 and SEQ ID NO:6 and complements thereof to at least a first target polynucleotide sequence; b) hybridizing a second pair of PCR primers selected from SEQ ID NO:7-8, SEQ ID NO:10-11, SEQ ID NO:13-14, SEQ ID NO:16-17, SEQ ID NO:19-20, SEQ ID NO:22-23, SEQ ID NO:25-26, SEQ ID NO:28-29, SEQ ID NO:31-32, SEQ ID NO:34-35, SEQ ID NO:37-38, SEQ ID NO:40-41, SEQ ID NO:43-44, SEQ ID NO:46-47, SEQ ID NO:49-50, SEQ ID NO:52-53, SEQ ID NO:55-56, SEQ ID NO:59 and SEQ ID NO:56, SEQ ID NO:61-62, SEQ ID NO:64-65, SEQ ID NO:67-68, SEQ ID NO:70-71, SEQ ID NO:73-74, SEQ ID NO:76-77, SEQ ID NO:79-80, SEQ ID NO:82-83, SEQ ID NO:85-86, and SEQ ID NO:88-89 and complements thereof to at least a second target polynucleotide sequence; c) amplifying said at least first and said at least second target polynucleotide sequences; and d) detecting said at least first and said at least second amplified target polynucleotide sequence products; wherein the detection of the at least first amplified target polynucleotide sequence product and the detection of the at least second amplified target polynucleotide sequence product is indicative of the presence of *E. coli* O157:H7 in the sample and not *E. coli* O55:H7.

In further embodiments, the assay further has a first probe of SEQ ID NO:3 and a second probe selected from SEQ ID NO:9, SEQ ID NO:12, SEQ ID NO:15, SEQ ID NO:18, SEQ ID NO:21, SEQ ID NO:24, SEQ ID NO:27 SEQ ID NO:30, SEQ ID NO:33, SEQ ID NO:36, SEQ ID NO:39, SEQ ID NO:42, SEQ ID NO:45, SEQ ID NO:48, SEQ ID NO:51, SEQ ID NO:54, SEQ ID NO:57, SEQ ID NO:58, SEQ ID NO:60, SEQ ID NO:63, SEQ ID NO:66, SEQ ID NO:69, SEQ ID NO:72, SEQ ID NO:75, SEQ ID NO:78, SEQ ID NO:81, SEQ ID NO:84, SEQ ID NO:87, and SEQ ID NO:90, the first probe further comprises a first label and said second probe further comprises a second label, wherein both labels are selected from a dye, a radioactive isotope, a chemiluminescent label, and an enzyme, the dye comprises a fluorescein dye, a rhodamine dye, or a cyanine dye, the dye is a fluorescein dye and first probe is labeled with FAM™ dye and said second probe is labeled with VIC® dye. The assay further has preparing the sample for PCR amplification prior to hybridizing, for example, but not limited to (1) bacterial enrichment, (2) separation of bacterial cells from the sample, (3) cell lysis, and (4) total DNA extraction, the sample can be for or a water sample, an environmental sample, and so on and the food sample comprises a selectively enriched food matrix. The assay can be by polymerase chain reaction, wherein hybridizing and amplifying of said first pair of polynucleotide primers occurs in a first vessel and said hybridizing and amplifying of said second pair of polynucleotide primers occurs in a second vessel, or hybridizing and amplifying of said first pair of polynucleotide primers and said hybridizing and amplifying of said second pair of polynucleotide primers occurs in a single vessel, the detection is a real-time assay, the real-time assay is a SYBR® Green dye assay or a TaqMan® assay.

In still another embodiment, the invention teaches a assay for the detection of *E. coli* O157:H7 in a sample comprising: a) hybridizing a first pair of PCR primers to a first target polynucleotide sequence within SEQ ID NO:111; b) hybridizing a second pair of PCR primers to a second target polynucleotide sequence within a sequence selected from SEQ ID NO:91-110; c) amplifying said at least first and said at least second target polynucleotide sequences; and d) detecting said at least first and said at least second amplified target polynucleotide sequence products; wherein the detection of the at least first amplified target polynucleotide sequence product and the detection of the at least second amplified target polynucleotide sequence product is indicative of the presence of *E. coli* O157:H7 in the sample and not *E. coli* O55:H7. The assay can further have a first probe of SEQ ID NO:3 and a second probe selected from SEQ ID NO:9, SEQ ID NO:12, SEQ ID NO:15, SEQ ID NO:18, SEQ ID NO:21, SEQ ID NO:24, SEQ ID NO:27 SEQ ID NO:30, SEQ ID NO:33, SEQ ID NO:36, SEQ ID NO:39, SEQ ID NO:42, SEQ ID NO:45, SEQ ID NO:48, SEQ ID NO:51, SEQ ID NO:54, SEQ ID NO:57, SEQ ID NO:58, SEQ ID NO:60, SEQ ID NO:63, SEQ ID NO:66, SEQ ID NO:69, SEQ ID NO:72, SEQ ID NO:75, SEQ ID NO:78, SEQ ID NO:81, SEQ ID NO:84, SEQ ID NO:87, and SEQ ID NO:90, the first probe further comprises a first label and said second probe further comprises a second label, wherein both labels are selected from a dye, a radioactive isotope, a chemiluminescent label, and an enzyme, the dye comprises a fluorescein dye, a rhodamine dye, or a cyanine dye, the dye is a fluorescein dye and first probe is labeled with FAM™ dye and said second probe is labeled with VIC® dye. The assay further has preparing the sample for PCR amplification prior to hybridizing, for example, but not limited to (1) bacterial enrichment, (2) separation of bacterial cells from the sample, (3) cell lysis, and (4) total DNA extraction, the sample can be for or a water sample, an environmental sample, and so on and the food sample comprises a selectively enriched food matrix. The assay can be by polymerase chain reaction, wherein hybridizing and amplifying of said first pair of polynucleotide primers occurs in a first vessel and said hybridizing and amplifying of said second pair of polynucleotide primers occurs in a second vessel, or hybridizing and amplifying of said first pair of polynucleotide primers and said hybridizing and amplifying of said second pair of polynucleotide primers occurs in a single vessel, the detection is a real-time assay, the real-time assay is a SYBR® Green dye assay or a TaqMan® assay.

In one embodiment, disclosed is a method for specifically detecting *E. coli* O157:H7, comprising: hybridizing at least a first pair of polynucleotide primers to at least a first target polynucleotide sequence, hybridizing at least a second pair of polynucleotide primers to at least a second target polynucleotide sequence, amplifying said at least first and said at least second target polynucleotide sequences, and detecting said at least first and said at least second amplified target polynucleotide sequence products, wherein the detection of the at least first amplified target polynucleotide sequence product and the detection of the at least second amplified target polynucleotide sequence product is indicative of the presence of *E. coli* O157:H7 in a sample and not *E. coli* O55:H7. The method further has preparing the sample for PCR amplification prior to hybridizing, for example, but not limited to (1) bacterial enrichment, (2) separation of bacterial cells from the sample, (3) cell lysis, and (4) total DNA extraction, the sample can be for or a water sample, an environmental sample, and so on and the food sample comprises a selectively enriched food matrix. The method can be by polymerase chain reaction, having at least a first probe and at least a second probe, said first probe further comprises a first label and said second probe further comprises a second label, both labels are selected from a dye, a radioactive isotope, a chemiluminescent label, and an enzyme, the dye comprises a fluorescein dye, a rhodamine dye, or a cyanine dye, the first probe is labeled with FAM™ dye and said second probe is labeled with VIC® dye, wherein hybridizing and amplifying of said first pair of polynucleotide primers occurs in a first vessel and said hybridizing and amplifying of said second pair of polynucleotide primers occurs in a second vessel, or hybridizing and amplifying of said first pair of polynucleotide primers and said hybridizing and amplifying of said second pair of polynucleotide primers occurs in a single vessel, the detection is a real-time assay, the real-time assay is a SYBR® Green dye assay or a TaqMan® assay. The method includes a first primer pair is selected from SEQ ID NO:1-2, SEQ ID NO:1 and SEQ ID NO:4, SEQ ID NO:1 and SEQ ID NO:5, and SEQ ID NO:1 and SEQ ID NO:6 and said second primer pair is selected from SEQ ID NO:7-8, SEQ ID NO:10-11, SEQ ID NO:13-14, SEQ ID NO:16-17, SEQ ID NO:19-20, SEQ ID NO:22-23, SEQ ID NO:25-26, SEQ ID NO:28-29, SEQ ID NO:31-32, SEQ ID NO:34-35, SEQ ID NO:37-38, SEQ ID NO:40-41, SEQ ID NO:43-44, SEQ ID NO:46-47, SEQ ID NO:49-50, SEQ ID NO:52-53, SEQ ID NO:55-56, SEQ ID NO:59 and SEQ ID NO:56, SEQ ID NO:61-62, SEQ ID NO:64-65, SEQ ID NO:67-68, SEQ ID NO:70-71, SEQ ID NO:73-74, SEQ ID NO:76-77, SEQ ID NO:79-80, SEQ ID NO:82-83, SEQ ID NO:85-86, and SEQ ID NO:88-89, and said first probe is SEQ ID NO:3 for use for said first primer pair and said second probe is selected according to FIG. 3 for use with said second primer pair from SEQ ID NO:9, SEQ ID NO:12, SEQ ID NO:15, SEQ ID NO:18, SEQ ID NO:21, SEQ ID NO:24, SEQ ID NO:27 SEQ ID NO:30, SEQ ID NO:33, SEQ ID NO:36, SEQ ID NO:39, SEQ ID NO:42, SEQ ID NO:45, SEQ ID NO:48, SEQ ID NO:51, SEQ ID NO:54, SEQ ID NO:57, SEQ ID NO:58, SEQ ID NO:60, SEQ ID NO:63, SEQ ID NO:66, SEQ ID NO:69, SEQ ID NO:72, SEQ ID NO:75, SEQ ID NO:78, SEQ ID NO:81, SEQ ID NO:84, SEQ ID NO:87, and SEQ ID NO:90, wherein said first target polynucleotide sequence is within SEQ ID NO:111 and said second target polynucleotide sequence is within the group selected from SEQ ID NO:91-110.

In another embodiment, disclosed is a polynucleotide sequence or its complement for the detection of *E. coli* O157:H7 and not *E. coli* O55:H7 identical to at least 16 contiguous polynucleotides from a first sequence selected from the group consisting of SEQ ID NO:90-110 and a second sequence of SEQ ID NO:111, the contiguous polynucleotide is a primer or a probe, the has a label selected from a dye, a radioactive isotope, a chemiluminescent label, and an enzyme, the dye comprises a fluorescein dye, a rhodamine dye, or a cyanine dye, including but not limited to FAM™ dye and VIC® dye, as exemplary dyes.

In another embodiment, disclosed is a kit for the detection of *E. coli* O157:H7 in a sample comprising a first pair of PCR primers selected from the group consisting of: SEQ ID NO:1-2, SEQ ID NO:1 and SEQ ID NO:4, SEQ ID NO:1 and SEQ ID NO:5, and SEQ ID NO:1 and SEQ ID NO:6; b) a second pair of PCR primers selected from SEQ ID NO:7-8, SEQ ID NO:10-11, SEQ ID NO:13-14, SEQ ID NO:16-17, SEQ ID NO:19-20, SEQ ID NO:22-23, SEQ ID NO:25-26, SEQ ID NO:28-29, SEQ ID NO:31-32, SEQ ID NO:34-35, SEQ ID NO:37-38, SEQ ID NO:40-41, SEQ ID NO:43-44, SEQ ID NO:46-47, SEQ ID NO:49-50, SEQ ID NO:52-53, SEQ ID NO:55-56, SEQ ID NO:59 and SEQ ID NO:56, SEQ ID NO:61-62, SEQ ID NO:64-65, SEQ ID NO:67-68, SEQ ID NO:70-71, SEQ ID NO:73-74, SEQ ID NO:76-77, SEQ ID NO:79-80, SEQ ID NO:82-83, SEQ ID NO:85-86, and SEQ ID NO:88-89; c) a polymerase; and optionally a first probe of SEQ ID NO:3 for use with selected said first pair of PCR primers and a second probe according to FIG. 3 for use with selected said second pair of PCR primers selected from SEQ ID NO:9, SEQ ID NO:12, SEQ ID NO:15, SEQ ID NO:18, SEQ ID NO:21, SEQ ID NO:24, SEQ ID NO:27 SEQ ID NO:30, SEQ ID NO:33, SEQ ID NO:36, SEQ ID NO:39, SEQ ID NO:42, SEQ ID NO:45, SEQ ID NO:48, SEQ ID NO:51, SEQ ID NO:54, SEQ ID NO:57, SEQ ID NO:58, SEQ ID NO:60, SEQ ID NO:63, SEQ ID NO:66, SEQ ID NO:69, SEQ ID NO:72, SEQ ID NO:75, SEQ ID NO:78, SEQ ID NO:81, SEQ ID NO:84, SEQ ID NO:87, and SEQ ID NO:90. The first probe further comprises a first label and said second probe further comprises a second label, both labels are selected from a dye, a radioactive isotope, a chemiluminescent label, and an enzyme, the dye comprises a fluorescein dye, a rhodamine dye, or a cyanine dye, and the first probe is labeled with FAM™ dye and said second probe is labeled with VIC® dye.

In the following description, certain aspects and embodiments will become evident. It should be understood that a given embodiment need not have all aspects and features described herein. It should be understood that these aspects and embodiments are merely exemplary and explanatory and are not restrictive of the invention.

It is to be understood that both the foregoing general description and the following detailed description are exemplary and explanatory only and are not restrictive of the invention, as claimed.

The accompanying figures, which are incorporated in and constitute a part of this specification, illustrate several exemplary embodiments of the disclosure and together with the description, serve to explain certain teachings.

There still exists a need for improved assays and methods for detecting and differentiating pathogenic organisms from non-pathogenic organisms which can be complicated by globally regional differences as well as by the need for improved sensitivity and specificity of detection.

These and other features of the present teachings are set forth herein.

DESCRIPTION OF THE DRAWINGS

The skilled artisan will understand that the drawings described below are for illustration purposes only. The drawings are not intended to limit the scope of the present teachings in any way.

FIG. 1 illustrates primer and probe sets useful in detecting SEQ ID NO:111.

FIG. 2 illustrates TaqMan® assay results for assays designed from SEQ ID NO:1-6 to detect SEQ ID NO:111, in accordance with various embodiments.

FIG. 3 illustrates a seven by nucleotide insertion unique to SEQ ID NO:111.

FIG. 4 illustrates primer and probe sets useful in detecting SEQ ID NO:90-110.

FIG. 5 illustrates the results of assays used for the specific detection of *E. coli* O157:H7 and not O55:H7.

DETAILED DESCRIPTION

For the purposes of interpreting of this specification, the following definitions will apply and whenever appropriate, terms used in the singular will also include the plural and vice versa. In the event that any definition set forth below conflicts with the usage of that word in any other document, including any document incorporated herein by reference, the definition set forth below shall always control for purposes of interpreting this specification and its associated claims unless a contrary meaning is clearly intended (for example in the document where the term is originally used). It is noted that, as used in this specification and the appended claims, the singular forms "a," "an," and "the," include plural referents unless expressly and unequivocally limited to one referent. The use of "or" means "and/or" unless stated otherwise. The use of "comprise," "comprises," "comprising," "include," "includes," and "including" are interchangeable and not intended to be limiting. Furthermore, where the description of one or more embodiments uses the term "comprising," those skilled in the art would understand that, in some specific instances, the embodiment or embodiments can be alternatively described using the language "consisting essentially of" and/or "consisting of"

Definitions:

As used herein, the phrase "nucleic acid," "oligonucleotide", and polynucleotide(s)" are interchangeable and not intended to be limiting.

Reference will now be made to various embodiments, examples of which are illustrated in the accompanying drawings.

As used herein, the phrase "stringent hybridization conditions" refers to hybridization conditions which can take place under a number of pH, salt and temperature conditions. The pH can vary from 6 to 9, preferably 6.8 to 8.5. The salt concentration can vary from 0.15 M sodium to 0.9 M sodium, and other cations can be used as long as the ionic strength is equivalent to that specified for sodium. The temperature of the hybridization reaction can vary from 30° C. to 80° C., preferably from 45° C. to 70° C. Additionally, other compounds can be added to a hybridization reaction to promote specific hybridization at lower temperatures, such as at or approaching room temperature. Among the compounds contemplated for lowering the temperature requirements is formamide. Thus, a polynucleotide is typically "substantially complementary" to a second polynucleotide if hybridization occurs between the polynucleotide and the second polynucleotide. As used herein, "specific hybridization" refers to hybridization between two polynucleotides under stringent hybridization conditions.

As used herein, the term "polynucleotide" refers to a polymeric form of nucleotides of any length, either ribonucleotides, deoxynucleotides, or peptide nucleic acids (PNA), and includes both double- and single-stranded RNA, DNA, and PNA. A polynucleotide may include nucleotide sequences having different functions, including, for instance, coding regions, and non-coding regions such as regulatory regions. A polynucleotide can be obtained directly from a natural source, or can be prepared with the aid of recombinant, enzymatic, or chemical techniques. A polynucleotide can be linear or circular in topology. A polynucleotide can be, for example, a portion of a vector, such as an expression or cloning vector, or a fragment. An "oligonucleotide" refers to a polynucleotide of the present invention, typically a primer and/or a probe.

As used herein a "target-specific polynucleotide" refers to a polynucleotide having a target-binding segment that is perfectly or substantially complementary to a target sequence, such that the polynucleotide binds specifically to an intended target without significant binding to non-target sequences under sufficiently stringent hybridization conditions. The target-specific polynucleotide can be e.g., a primer or probe and the subject of hybridization with its complementary target sequence.

The term "target sequence", "target nucleic acid", "target" or "target polynucleotide sequence" refers to a nucleic acid of interest. The target sequence can be a polynucleotide sequence that is the subject of hybridization with a complementary polynucleotide, e.g. a primer or probe. The target sequence can be composed of DNA, RNA, an analog thereof, and including combinations thereof. The target sequence may be known or not known, in terms of its actual sequence and its amplification can be desired. The target sequence may or may not be of biological significance. Typically, though not always, it is the significance of the target sequence which is being studied in a particular experiment. As non-limiting examples, target sequences may include regions of genomic DNA, regions of genomic DNA which are believed to contain one or more polymorphic sites, DNA encoding or believed to encode genes or portions of genes of known or unknown function, DNA encoding or believed to encode proteins or portions of proteins of known or unknown function, DNA encoding or believed to encode regulatory regions such as promoter sequences, splicing signals, polyadenylation signals, etc.

As used herein an "amplified target polynucleotide sequence product" refers to the resulting amplicon from an amplification reaction such as a polymerase chain reaction. The resulting amplicon product arises from hybridization of complementary primers to a target polynucleotide sequence under suitable hybridization conditions and the repeating in a cyclic manner the polymerase chain reaction as catalyzed by DNA polymerase for DNA amplification or RNA polymerase for RNA amplification.

As used herein, the "polymerase chain reaction" or PCR is a an amplification of nucleic acid consisting of an initial denaturation step which separates the strands of a double stranded nucleic acid sample, followed by repetition of (i) an annealing step, which allows amplification primers to anneal specifically to positions flanking a target sequence; (ii) an extension step which extends the primers in a 5' to 3' direction thereby forming an amplicon polynucleotide complementary to the target sequence, and (iii) a denaturation step which causes the separation of the amplicon from the target sequence (Mullis et al., eds, The Polymerase Chain Reaction, BirkHauser, Boston, Mass. (1994). Each of the above steps may be conducted at a different temperature, preferably using an automated thermocycler (Applied Biosystems LLC, a division of Life Technologies Corporation, Foster City, Calif.). If desired, RNA samples can be converted to DNA/RNA heteroduplexes or to duplex cDNA by methods known to one of skill in the art.

As used herein, "amplifying" and "amplification" refers to a broad range of techniques for increasing polynucleotide sequences, either linearly or exponentially. Exemplary amplification techniques include, but are not limited to, PCR or any other method employing a primer extension step. Other non-limiting examples of amplification include, but are not limited to, ligase detection reaction (LDR) and ligase chain reaction (LCR). Amplification methods may comprise thermal-cycling or may be performed isothermally. In various embodiments, the term "amplification product" includes products from any number of cycles of amplification reactions.

In certain embodiments, amplification methods comprise at least one cycle of amplification, for example, but not limited to, the sequential procedures of: hybridizing primers to primer-specific portions of target sequence or amplification products from any number of cycles of an amplification reaction; synthesizing a strand of nucleotides in a template-dependent manner using a polymerase; and denaturing the newly-formed nucleic acid duplex to separate the strands. The cycle may or may not be repeated.

Descriptions of certain amplification techniques can be found, among other places, in H. Ehrlich et al., Science, 252:1643-50 (1991), M. Innis et al., PCR Protocols: A Guide to Methods and Applications, Academic Press, New York, N.Y. (1990), R. Favis et al., Nature Biotechnology 18:561-64 (2000), and H. F. Rabenau et al., Infection 28:97-102 (2000); Sambrook and Russell, Molecular Cloning, Third Edition, Cold Spring Harbor Press (2000) (hereinafter "Sambrook and Russell"), Ausubel et al., Current Protocols in Molecular Biology (1993) including supplements through September 2005, John Wiley & Sons (hereinafter "Ausubel et al.").

The term "label" refers to any moiety which can be attached to a molecule and: (i) provides a detectable signal; (ii) interacts with a second label to modify the detectable signal provided by the second label, e.g. FRET; (iii) stabilizes hybridization, i.e. duplex formation; or (iv) provides a capture moiety, i.e. affinity, antibody/antigen, ionic complexation. Labelling can be accomplished using any one of a large number of known techniques employing known labels, linkages, linking groups, reagents, reaction conditions, and analysis and purification methods. Labels include light-emitting compounds which generate a detectable signal by fluorescence, chemiluminescence, or bioluminescence (Kricka, L. in Nonisotopic DNA Probe Techniques (1992), Academic Press, San Diego, pp. 3-28). Another class of labels are hybridization-stabilizing moieties which serve to enhance, stabilize, or influence hybridization of duplexes, e.g. intercalators, minor-groove binders, and cross-linking functional groups (Blackburn, G. and Gait, M. Eds. "DNA and RNA structure" in Nucleic Acids in Chemistry and Biology, 2.sup.nd Edition, (1996) Oxford University Press, pp. 15-81). Yet another class of labels effect the separation or immobilization of a molecule by specific or non-specific capture, for example biotin, digoxigenin, and other haptens (Andrus, A. "Chemical methods for 5' non-isotopic labelling of PCR probes and primers" (1995) in PCR 2: A Practical Approach, Oxford University Press, Oxford, pp. 39-54).

The terms "annealing" and "hybridization" are used interchangeably and mean the base-pairing interaction of one nucleic acid with another nucleic acid that results in formation of a duplex or other higher-ordered structure. The primary interaction is base specific, i.e. A/T and G/C, by Watson/Crick and Hoogsteen-type hydrogen bonding.

The term "end-point analysis" refers to a method where data collection occurs only when a reaction is substantially complete.

The term "real-time analysis" refers to periodic monitoring during PCR. Certain systems such as the ABI 7700 Sequence Detection System (Applied Biosystems, Foster City, Calif.) conduct monitoring during each thermal cycle at a pre-determined or user-defined point. Real-time analysis of PCR with FRET probes measures fluorescent dye signal changes from cycle-to-cycle, preferably minus any internal control signals.

The term "quenching" refers to a decrease in fluorescence of a first moiety (reporter dye) caused by a second moiety (quencher) regardless of the mechanism.

A "primer," as used herein, is an oligonucleotide that is complementary to a portion of target polynucleotide and, after hybridization to the target polynucleotide, may serve as a starting-point for an amplification reaction and the synthesis of an amplification product. Primers include, but are not limited to, spanning primers. A "primer pair" refers to two primers that can be used together for an amplification reaction. A "PCR primer" refers to a primer in a set of at least two primers that are capable of exponentially amplifying a target nucleic acid sequence in the polymerase chain reaction.

The term "probe" comprises a polynucleotide that comprises a specific portion designed to hybridize in a sequence-specific manner with a complementary region of a specific nucleic acid sequence, e.g., a target nucleic acid sequence. In certain embodiments, the specific portion of the probe may be specific for a particular sequence, or alternatively, may be degenerate, e.g., specific for a set of sequences. In certain embodiments, the probe is labeled. The probe can be an oligonucleotide that is complementary to at least a portion of an amplification product formed using two primers.

The terms "complement" and "complementary" as used herein, refer to the ability of two single stranded polynucleotides (for instance, a primer and a target polynucleotide) to base pair with each other, where an adenine on one strand of a polynucleotide will base pair to a thymine or uracil on a strand of a second polynucleotide and a cytosine on one strand of a polynucleotide will base pair to a guanine on a strand of a second polynucleotide. Two polynucleotides are complementary to each other when a nucleotide sequence in one polynucleotide can base pair with a nucleotide sequence in a second polynucleotide. For instance, 5'-ATGC and 5'-GCAT are complementary.

A "label" refers to a moiety attached (covalently or non-covalently), or capable of being attached, to an oligonucleotide, which provides or is capable of providing information about the oligonucleotide (e.g., descriptive or identifying information about the oligonucleotide) or another polynucleotide with which the labeled oligonucleotide interacts (e.g., hybridizes). Labels can be used to provide a detectable (and optionally quantifiable) signal. Labels can also be used to attach an oligonucleotide to a surface.

A "fluorophore" is a moiety that can emit light of a particular wavelength following absorbance of light of shorter wavelength. The wavelength of the light emitted by a particular fluorophore is characteristic of that fluorophore. Thus, a particular fluorophore can be detected by detecting light of an appropriate wavelength following excitation of the fluorophore with light of shorter wavelength.

The term "quencher" as used herein refers to a moiety that absorbs energy emitted from a fluorophore, or otherwise interferes with the ability of the fluorescent dye to emit light. A quencher can re-emit the energy absorbed from a fluorophore in a signal characteristic for that quencher, and thus a quencher can also act as a fluorophore (a fluorescent quencher). This phenomenon is generally known as fluorescent resonance energy transfer (FRET). Alternatively, a quencher can dissipate the energy absorbed from a fluorophore as heat (a non-fluorescent quencher).

As used herein, a "sample" refers to any substance comprising nucleic acid material. A sample to be tested and can include food intended for human or animal consumption such as meat, nuts, legumes, fruit, and vegetables, a beverage sample, a fermentation broth, a forensic sample, an environmental sample (e.g., soil, dirt, garbage, sewage, air, or water), including food processing and manufacturing surfaces, or a biological sample. A "biological sample" refers to a sample obtained from eukaryotic or prokaryotic sources. Examples of eukaryotic sources include mammals, such as a human or a cow or a member of the family Muridae (a murine animal such as rat or mouse). Alternatively, the sample may include blood, urine, feces, or other materials from a human or a livestock animal. The sample may be tested directly, or may be treated in some manner prior to testing. For example, the sample may be subjected to PCR amplification using appropriate oligonucleotide primers. Examples of prokaryotic sources include enterococci. The biological sample can be, for instance, in the form of a single cell, in the form of a tissue, or in the form of a fluid.

As used herein, "detecting" or "detection" refers to the disclosure or revelation of the presence or absence in a sample of a target polynucleotide sequence or amplified target polynucleotide sequence product. The detecting can be by end point, real-time, enzymatic, and by resolving the amplification product on a gel and determining whether the expected amplification product is present, or other methods known to one of skill in the art.

The presence or absence of an amplified product can be determined or its amount measured. Detecting an amplified product can be conducted by standard methods well known in the art and used routinely. The detecting may occur, for instance, after multiple amplification cycles have been run (typically referred to an end-point analysis), or during each amplification cycle (typically referred to as real-time). Detecting an amplification product after multiple amplification cycles have been run is easily accomplished by, for instance, resolving the amplification product on a gel and determining whether the expected amplification product is present. In order to facilitate real-time detection or quantification of the amplification products, one or more of the primers and/or probes used in the amplification reaction can be labeled, and various formats are available for generating a detectable signal that indicates an amplification product is present. For example, a convenient label is typically a label that is fluorescent, which may be used in various formats including, but are not limited to, the use of donor fluorophore labels, acceptor fluorophore labels, fluorophores, quenchers, and combinations thereof. Assays using these various formats may include the use of one or more primers that are labeled (for instance, scorpions primers, amplifluor primers), one or more probes that are labeled (for instance, adjacent probes, TaqMan® probes, light-up probes, molecular beacons), or a combination thereof. The skilled person will understand that in addition to these known formats, new types of formats are routinely disclosed. The present invention is not limited by the type of method or the types of probes and/or primers used to detect an amplified product. Using appropriate labels (for example, different fluorophores) it is possible to combine (multiplex) the results of several different primer pairs (and, optionally, probes if they are present) in a single reaction. As an alternative to detection using a labeled primer and/or probe, an amplification product can be detected using a polynucleotide binding dye such as a fluorescent DNA binding dye. Examples include, for instance, SYBR® Green dye or SYBR® Gold dye (Molecular Probes). Upon interaction with the double-stranded amplification product, such polynucleotide binding dyes emit a fluorescence signal after excitation with light at a suitable wavelength. A polynucleotide binding dye such as a polynucleotide intercalating dye also can be used.

As used herein, an "*E. coli* O157:H7-specific nucleotide probe" refers to a sequence that is able to specifically hybridize to an *E. coli* O157:H7 target sequence present in a sample containing *E. coli* O157:H7 under suitable hybridization conditions and which does not hybridize with DNA from other *E. coli* strains or from other bacterial species. It is well within the ability of one skilled in the art to determine suitable hybridization conditions based on probe length, G+C content, and the degree of stringency required for a particular application.

It is expected that minor sequence variations in *E. coli* O157:H7-specific nucleotide sequences associated with nucleotide additions, deletions and mutations, whether naturally occurring or introduced in vitro, would not interfere with the usefulness of SEQ ID NO:1-111 in the detection of enterohemorrhagic *E. coli* (EHEC), in methods for preventing EHEC infection, and in methods for treating EHEC infection, as would be understood by one of skill in the art. Therefore, the scope of the present invention as claimed is intended to encompass minor variations in the sequences of SEQ ID NO:1-111 and sequences having at least 90% homology to the SEQ ID NO:1-111 sequences.

The probe may be RNA or DNA. Depending on the detection means employed, the probe may be unlabeled, radiolabeled, chemiluminescent labeled, enzyme labeled, or labeled with a dye. The probe may be hybridized with a sample in solution or immobilized on a solid support such as nitrocellulose, a microarray or a nylon membrane, or the probe may be immobilized on a solid support, such as a silicon chip or a microarray.

Conditions that "allow" an event to occur or conditions that are "suitable" for an event to occur, such as hybridization, strand extension, and the like, or "suitable" conditions are conditions that do not prevent such events from occurring. Thus, these conditions permit, enhance, facilitate, and/or are conducive to the event. Such conditions, known in the art and described herein, may depend upon, for example, the nature of the nucleotide sequence, temperature, and buffer conditions. These conditions may also depend on what event is desired, such as hybridization, cleavage, or strand extension. An "isolated" polynucleotide refers to a polynucleotide that has been removed from its natural environment. A "purified" polynucleotide is one that is at least about 60% free, preferably at least about 75% free, and most preferably at least about 90% free from other components with which they are naturally associated.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims. Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.). The term "and/or" means one or all of the listed elements or a combination of any two or more of the listed elements.

There are many known methods of amplifying nucleic acid sequences including e.g., PCR. See, e.g., PCR Technology: Principles and Applications for DNA Amplification (ed. H. A. Erlich, Freeman Press, NY, N.Y., 1992); PCR Protocols: A Guide to Methods and Applications (eds. Innis, et al., Academic Press, San Diego, Calif., 1990); Mattila et al., Nucleic Acids Res. 19, 4967 (1991); Eckert et al., PCR Methods and Applications 1, 17 (1991); PCR (eds. McPherson et al., IRL Press, Oxford); and U.S. Pat. Nos. 4,683,202, 4,683,195, 4,800,159 4,965,188 and 5,333,675 each of which is incorporated herein by reference in their entireties for all purposes.

Nucleic acid amplification techniques are traditionally classified according to the temperature requirements of the amplification process. Isothermal amplifications are conducted at a constant temperature, in contrast to amplifications that require cycling between high and low temperatures. Examples of isothermal amplification techniques are: Strand Displacement Amplification (SDA; Walker et al., 1992, Proc. Natl. Acad. Sci. USA 89:392 396; Walker et al., 1992, Nuc. Acids. Res. 20:1691 1696; and EP 0 497 272, all of which are incorporated herein by reference), self-sustained sequence replication (3SR; Guatelli et al., 1990, Proc. Natl. Acad. Sci. USA 87:1874 1878), the Q.beta. replicase system (Lizardi et al., 1988, BioTechnology 6:1197 1202), and the techniques disclosed in WO 90/10064 and WO 91/03573.

Examples of techniques that require temperature cycling are: polymerase chain reaction (PCR; Saiki et al., 1985, Science 230:1350 1354), ligase chain reaction (LCR; Wu et al., 1989, Genomics 4:560 569; Barringer et al., 1990, Gene 89:117 122; Barany, 1991, Proc. Natl. Acad. Sci. USA 88:189 193), transcription-based amplification (Kwoh et al., 1989, Proc. Natl. Acad. Sci. USA 86:1173 1177) and restriction amplification (U.S. Pat. No. 5,102,784).

Other exemplary techniques include Nucleic Acid Sequence-Based Amplification ("NASBA"; see U.S. Pat. No. 5,130,238), Q.beta. replicase system (see Lizardi et al., BioTechnology 6:1197 (1988)), and Rolling Circle Amplification (see Lizardi et al., Nat Genet. 19:225 232 (1998)). The amplification primers of the present invention may be used to carry out, for example, but not limited to, PCR, SDA or tSDA. Any of the amplification techniques and methods disclosed herein can be used to practice the claimed invention as would be understood by one of ordinary skill in the art.

PCR is an extremely powerful technique for amplifying specific polynucleotide sequences, including genomic DNA, single-stranded cDNA, and mRNA among others. Various methods of conducting PCR amplification and primer design and construction for PCR amplification will be known to those of skill in the art. Generally, in PCR a double-stranded DNA to be amplified is denatured by heating the sample. New DNA synthesis is then primed by hybridizing primers to the target sequence in the presence of DNA polymerase and excess dNTPs. In subsequent cycles, the primers hybridize to the newly synthesized DNA to produce discreet products with the primer sequences at either end. The products accumulate exponentially with each successive round of amplification.

The DNA polymerase used in PCR is often a thermostable polymerase. This allows the enzyme to continue functioning after repeated cycles of heating necessary to denature the double-stranded DNA. Polymerases that are useful for PCR include, for example, Taq DNA polymerase, Tth DNA polymerase, Tfl DNA polymerase, Tma DNA polymerase, Tli DNA polymerase, and Pfu DNA polymerase. There are many commercially available modified forms of these enzymes including: AmpliTaq® and AmpliTaq Gold® both available from Applied Biosystems. Many are available with or without a 3- to 5' proofreading exonuclease activity. See, for example, Vent® and Vent®. (exo-) available from New England Biolabs.

Other suitable amplification methods include the ligase chain reaction (LCR) (e.g., Wu and Wallace, Genomics 4, 560 (1989) and Landegren et al., Science 241, 1077 (1988)), transcription amplification (Kwoh et al., Proc. Natl. Acad.

Sci. USA 86, 1173 (1989)), and self-sustained sequence replication (Guatelli et al., Proc. Nat. Acad. Sci. USA, 87, 1874 (1990)) and nucleic acid based sequence amplification (NABSA). (See, U.S. Pat. Nos. 5,409,818, 5,554,517, and 6,063,603). The latter two amplification methods include isothermal reactions based on isothermal transcription, which produce both single-stranded RNA (ssRNA) and double-stranded DNA (dsDNA) as the amplification products in a ratio of about 30 or 100 to 1, respectively.

Amplicon Selection:

Detection of *E. coli* O157:H7 by the use of the polymerase chain reaction provides a rapid method for detection. Moreover, the primer(s) (and probe used in a real-time PCR reaction) is desired to be specific and sensitive for only the organism of interest, i.e., *E. coli* O157:H7. However, the genome of *E. coli* O157:H7 is very similar to other *E. coli* genomes, both those which are disease causing (i.e., infectious) and pathogenic (ability to cause damage) e.g., serotype O55:H7 and those which are not pathogenic, e.g., serotype K12. Therefore, in one embodiment, the identification and selection of genomic sequence from *E. coli* O157:H7 (e.g., strain EDL993, GenBank Accession No. AE005174, Perna, N. T., et al., (2001) Nature 409(25):529-533) for the design of real-time PCR assays is based on the differential identification of *E. coli* O157:H7 genomic sequence (I, inclusion set) not found in closely related strains of *E. coli* (E, exclusion set). By identifying sequences not found in both infections and non-infectious strains of *E. coli*, target sequences specific to *E. coli* O157:H7 can be identified for primer design that do not, or only with rare exception, detect closely related *E. coli* strains and therefore identify *E. coli* O157:H7 with specificity and sensitivity.

Identification of *E. coli* O157:H7 Unique Sequence Regions:

The *E. coli* O157:H7 strain EDL933 genome has about 5.6 million base pairs (Mb) of DNA in the backbone sequence. When compared to a common, non-pathogenic laboratory strain, *E. coli* K12 strain MG1655, having about 4.6 Mb of DNA. Each genome has regions of DNA unique to one strain or the other, numbering in the hundreds of regions.

Prior to the claimed invention 'O-islands' where described as nucleic acid sequence regions unique to and found only in the O157:H7 serotype. O-islands regions total 1.34 megabases and 1,387 genes whereas 'K-islands' are described as being unique to serotype K12, totaling 0.53 megabases and 528 genes. (Perna, N. T., et al., supra). The design of assays specific for the O157:H7 serotype as described herein refutes the uniqueness of O-islands to only the O157:H7 serotype. Comparison of the genome of O157:H7 with that of O55:H7 unexpectedly revealed that the O55:H7 serotype also contained O-islands virtually identical to those of O157:H7. Therefore, prior to the claimed invention, a definitive identification of O157:H7 was difficult due to genome sequence similarity, even in supposedly serotype specific regions. The present invention as claimed has identified serotype unique DNA sequences for *E. coli* O157:H7 which were utilized for assay design and the subsequent detection of *E. coli* O157:H7 and not O55:H7 by PCR, hybridization and other molecular biology techniques as known to one skilled in the art.

The sequence of the *E. coli* O157:H7 genome is represented in public databases such as GenBank (NCBI, National Library of Medicine, The National Institutes of Health, Bethesda, Md.) EMBL, and DDBJ. One of skill in the art quickly recognizes that the genomic sequence of O157:H7 serotype is representative of a variety of non-O157:H7, yet pathogenic serotypes such as O111:H7, O26:H11 and O103:H2. A bioinformatic approach to identify *E. coli* O157:H7 unique sequence regions was undertaken and evaluated by Sanger sequencing and real-time PCR assays.

In one embodiment of the current teachings bioinformatic and direct DNA sequencing comparisons were conducted in an effort to identify *E. coli* O157:H7 serotype-specific sequences. 28 separate *E. coli* O157:H7 serotype EDL933 (GenBank Acc No. AE005174) O-island sequence regions were downloaded from the NCBI database GenBank, release 160). These O-islands were known to be present, absent in some or variants of O-islands in *E. coli* O157:H7. Additional O-island and K-island regions were sequenced by the Sanger/capillary electrophoresis method known to one of skill in the art from the Applied Biosystems microbial DNA collection of *E. coli* serotypes O157:H7, K12 and others. Alignment of the sequenced regions using algorithms known to one of ordinary skill in the art identified no O157:H7 "unique" regions. PCR primer pairs were designed for each of the 28 regions to specifically amplify the unique sequences within the O-islands against both inclusion (organism to be detected, i.e., *E. coli* O157:H7) and exclusion genomes (organisms not to be detected, i.e., *E. coli* non-O157:H7 serotypes and *Shigella* spp.) within the Applied Biosystems microbial DNA collection. The resulting amplification products were then sequenced and aligned to the EDL933 genome. Comparison of the alignments of the O157:H7 specific regions to non-O157:H7 sequences identified an *E. coli* O157:H7 sequence region (SEQ ID NO:111) that was used for the identification of *E. coli* O157:H7 antigen specific strains. PCR primer pairs (and probes for use in real-time PCR assays) were designed to the O157:H7 specific region and screened against ground beef. Any assay having a positive result indicated the assay cross-reacted with ground beef and was removed from further analyses. As shown in FIG. 1, the remaining PCR primer pairs and probes (SEQ ID NOs:1-6) were used in real-time PCR assays and evaluated against the Applied Biosystems microbial DNA collection (FIG. 2). For example, primer pairs SEQ ID NO:1-2, SEQ ID NO:1 and SEQ ID NO:4, SEQ ID NO:1 and SEQ ID NO:5, and SEQ ID NO:1 and SEQ ID NO:6 can be used for end-point analysis and when used in conjunction with SEQ ID NO:3 as the probe comprised the real-time PCR assays as listed in FIG. 1.

The primers and probes from FIG. 1 were used in real-time PCR assays on DNA extracts from various strains from the Applied Biosystems microbial DNA collection and have experimentally demonstrated the specificity of each assay for identification of *E. coli* O157:H7 and a weak signal for *E. coli* O55:H7 (FIG. 2), an unexpected result. A $C_t$ value >35 was consider a "weak positive" result. When a $C_t$ value is present a signal was detected, a positive result and 'no signal' indicates no detectable signal, and so a negative result. In all selected serotypes shown, the internal positive control had a detectable signal/positive result (data not shown).

As shown in FIG. 3, this region of the O157:H7 genome has a seven basepair insertion (a direct repeat) that is not present in O55:H7. This seven basepair insertion in O157:H7 relative to O55:H7 is the only significant sequence difference found between the two serotypes in SEQ ID NO:111. The forward primer of assay 18158 overlaps this insertion, which provides some specificity for O157:H7. Analysis of GenBank sequences for the SEQ ID NO:111 region indicted that the full-length sequence of SEQ ID 111 is found only in *E. coli* O157:H7, *Shigella sonnei*, and *Shigella boydii*. In all cases except O157:H7, the seven nucleotide O157:H7-specific insertion is absent. Other fragments of SEQ ID 111 that are more widely conserved among *E. coli* are nucleotide sequence positions 355 to 456, and 156 to 238. The 355-456 fragment overlaps the reverse primer of assay 18158, and partially overlaps the probe, but not the forward primer, which can account for the 18158 assay not detecting more serotypes.

These assays have been shown to be very specific for the rapid detection of *E. coli* O157:H7 and weakly positive for *E. coli* O55:H7 from isolated DNA and from ground beef samples. Experimental results confirmed that these assays have 100% sequence identity to the O157:H7 genome. Bioinformatic evidence indicated that the assays were specific for O157:H7 EDL933 and O157:H7 Sakai genomes, GenBank Accession Nos. AE005174 and NC_002695.1, respectively.

In another embodiment of the current teachings bioinformatic and direct DNA sequencing comparisons were conducted in an effort to identify sequences common to *E. coli* O157:H7 strains but absent or highly divergent in *E. coli* strains within the exclusion set. 14 *E. coli* O157:H7 genome sequences and 30 non-O157:H7 *E. coli* and *Shigella* spp. were downloaded from public databases (NCBI database GenBank, release 161.0, or the Sanger Center's public FTP site (Wellcome Trust Sanger Institute). The bioinformatic approach entailed aligning each of the 45 sequences against an *E. coli* O157:H7 reference genome (GenBank Accession No. NC_002695.1). The alignments and parsed results from the initial genome comparisons resulted in identifying 157 O157:H7 unique regions. These regions were then analyzed by BLASTN against the GenBank non-redundant database (nr). Sequences with at least 80% similarity over 50 or more contiguous nucleotides were removed from further analysis. Of those removed about two thirds of hits with more than 85% sequence identity were from strains of *E. coli*, *Shigella* or *E. fergusonii* for which whole genome sequence was not available. The remain ⅓ were to *Enterobacter*, *Salmonella* or *Erwina*. The resulting set of 118 O157:H7 unique regions were considered target sequences totaling 117 kb. Assays were designed from unique *E. coli* O157:H7 sequence regions which were identified by alignment of genomes.

The nearest neighbor of *E. coli* O157:H7 is *E. coli* O55:H7. Our sequencing in *E. coli* O55:H7 strains for known *E. coli* O157:H7 O-islands further supported the close relationship between the two serotypes as most O-islands were conserved between the two serotypes. Further genomic sequencing of the O55:H7 genome (PE704 isolate) in parallel with the sequencing of an O157:H7 strain (PE30 isolate) also supported the very close relationship of the two serotypes as single nucleotide polymorphisms (SNPs) in O55:H7 verse O157:H7 was only 0.28% (data not shown).

The 118 target sequences for O157:H7 were screened against the O55:H7 consensus genome assembly using BLASTN. Only 9.9 kb or 8.5% of the candidate O157:H7-specific sequence identified by genome comparison was found to be absent from the O55:H7 genome. 20 target sequences were found to be absent from the O55:H7 genome and all 20 had at least 98.85% sequence identity between any pair of the 15 publicly available O157:H7 genomes indicating each target sequence was highly conserved and assays designed from these regions would be highly indicative of *E. coli* O157:H7 strains and not O55:H7.

The 20 target sequences corresponded to seven regions identified in U.S. Pat. No. 6,365,723, incorporated herein by reference in its entirety. As indicated in Table 1, these regions are associated with CP933-M,N,X and P, cryptic prophages, each having a collection of open reading frames, and fimbrial proteins. For example, primer pairs SEQ ID NO:7-8, SEQ ID NO:10-11, SEQ ID NO:13-14, SEQ ID NO:16-17, SEQ ID NO:19-20, SEQ ID NO:22-23, SEQ ID NO:25-26, SEQ ID NO:28-29, SEQ ID NO:31-32, SEQ ID NO:34-35, SEQ ID NO:37-38, SEQ ID NO:40-41, SEQ ID NO:43-44, SEQ ID NO:46-47, SEQ ID NO:49-50, SEQ ID NO:52-53, SEQ ID NO:55-56, SEQ ID NO:59 and SEQ ID NO:56, SEQ ID NO:61-62, SEQ ID NO:64-65, SEQ ID NO:67-68, SEQ ID NO:70-71, SEQ ID NO:73-74, SEQ ID NO:76-77, SEQ ID NO:79-80, SEQ ID NO:82-83, SEQ ID NO:85-86, and SEQ ID NO:88-89 can be used for end-point analysis and when used in conjunction with a probe of SEQ ID NO:9, SEQ ID NO:12, SEQ ID NO:15, SEQ ID NO:18, SEQ ID NO:21, SEQ ID NO:24, SEQ ID NO:27 SEQ ID NO:30, SEQ ID NO:33, SEQ ID NO:36, SEQ ID NO:39, SEQ ID NO:42, SEQ ID NO:45, SEQ ID NO:48, SEQ ID NO:51, SEQ ID NO:54, SEQ ID NO:57, SEQ ID NO:58, SEQ ID NO:60, SEQ ID NO:63, SEQ ID NO:66, SEQ ID NO:69, SEQ ID NO:72, SEQ ID NO:75, SEQ ID NO:78, SEQ ID NO:81, SEQ ID NO:84, SEQ ID NO:87, or SEQ ID NO:90 as listed in FIG. 4, comprise real-time PCR assays. These 20 target sequences (SEQ ID NO:91-110) were used in the design of O157:H7-specific real-time PCR assays using algorithms known by one of skill in the art (FIG. 4). The 29 assays map to the seven regions as indicated in Table 1.

TABLE 1

*E. coli* O157:H7-specific genomic regions[a]

| Region number | EDL933 start | EDL933 end | Length (nt) | ORFs | Features |
|---|---|---|---|---|---|
| 1 | 1255352 | 1256121 | 770 | Z1328, Z1329 | CP933-M |
| 2 | 1256573 | 1257839 | 1267 | Z1332-Z1334 | CP933-M |
| 3 | 1262147 | 1263665 | 1519 | Z1341 | CP933-M |
| 4* | 1635627 | 1635757 | 131 | Z1781 | CP933-N |
| 5 | 1744789 | 1747582 | 2794 | Z1921-Z1924 | CP933-X |
| 6* | 2319451 | 2319578 | 128 | Z6065 | CP933-P |
| 7 | 2933425 | 2934070 | 646 | Z3276 | Fimbrial protein |

[a] as mapped to GenBank Acc. No. AE005174
*Regions 4 and 6 are duplicate copies of the same sequence.

Real-time PCR assays were designed from seven unique and specific *E. coli* O157:H7 sequence regions. The assays were then tested against the Applied Biosystems microbial DNA collection of *E. coli* strains and serotypes to confirm the specificity, sensitivity and unambiguous detection of only *E. coli* O157:H7 nucleic acid. However, unexpectedly, the selected assays also amplified nucleic acid from one strain of *E. coli* O103:H2 serotype and only one of four strains of the *E. coli* O26:H11 serotype. Subsequent testing revealed that the positive results for only one *E. coli* O26:H11 sample indicated mistyping of the sample.

In one embodiment, combining the results of an assay that detects a target polynucleotide sequence of SEQ ID NO:111 with the results of an assay that detects a target polynucleotide sequence selected from SEQ ID NO:91-110 provides specific and definitive detection for *E. coli* O157:H7 and not O55:H7. As shown in Table 2, the combination of assay Nos. 18158 and 19055 whether in single or duplex assay format provides an unambiguous positive test for *E. coli* O157:H7, i.e., a positive test for O157:H7 in each assay confirms a positive test for *E. coli* O157:H7.

TABLE 2

| Serotype | Assay No. 18158 | Assay No. 19055 | Interpreted result |
|---|---|---|---|
| O157:H7 (all) | + | + | Positive |
| O55:H7 (all) | weak + | − | − |
| O103:H2 (1/1) | − | + | − |
| O26:H11 (1/4) | − | + | − |

Clearly, neither assay alone is definitive for a single serotype of *E. coli* due to genomic similarity between the genomic regions of other *E. coli* serotypes. Yet, when two assays, as example, but not limited to the assays of Table 2, are used either in parallel or as a multiplex assay, e.g., in a real-time TaqMan® assay, for example, where each probe in each of the two assays has a different label for distinguishing results on a real-time PCR instrument, e.g., a 7500 Fast Real-Time PCR System (Applied Biosystems), a positive result from each assay is indicative of only *E. coli* O157:H7. Thus, without knowledge of genomic regions shared by serotype O157:H7 and O55:H7, design of an unambiguous, specific and sensitive test for *E. coli* O157:H7 would not be possible.

The claimed method to identify *E. coli* O157:H7 results from a two-pronged approach to identify target sequences for O157:H7 that do not also detect closely related either pathogenic or non-pathogenic *E. coli*. The identified *E. coli* O157:H7 target sequences were used to design primers and probes for real-time PCR assays. Programs known to one of skill in the art for assay design include Primer3 (Steve Rozen and Helen J. Skaletsky (2000) "Primer3" on the World Wide Web for general users and for biologist programmers as published in: Krawetz S, Misener S (eds) Bioinformatics Methods and Protocols: Methods in Molecular Biology. Humana Press, Totowa, N.J., pp 365-386), Primer Express® software (Applied Biosystems), and OLIGO 7 (Wojciech Rychlik (2007). "OLIGO 7 Primer Analysis Software". *Methods Mol. Biol.* 402: 35-60). The subsequently designed PCR primers and probes for use in assays by real-time PCR detected unambiguously, specifically and with great sensitivity *E. coli* O157:H7 and not O55:H7.

An assay from FIG. 2 along with an assay from FIG. 3 either in the same reaction vessel as a duplex (multiplex) assay or in separate reaction vessels have experimentally demonstrated the specificity of the dual-assay approach for identification of *E. coli* O157:H7 and the ability to distinguish O157:H7 from *E. coli* O55:H7 (Example 2). The results were also confirmed by sequencing various isolates of both serotypes O157:H7 and O55:H7. As indicated in FIG. 5, the results of real-time PCR analyses on DNA extracts from various matrix samples and various strains from the Applied Biosystems microbial DNA collection. When a $C_t$ value is present a signal was detected, a positive result and 'no result' indicates no signal detected, a negative result. A $C_t$ value >35 was determined to be a "weak positive". Both assays having a detected signal for O157:H7 were a positive identification of *E. coli* O157:H7. When at least one or both assays have no signal for O157:H7, the result is considered negative for *E. coli* O157:H7. In all selected serotypes shown, the internal positive control had a detectable signal/positive result.

The rare signal detected from a serotype other than *E. coli* O157:H7 was unexpected for the dual/multiplex assay. The likelihood of the simultaneous presence of a rare serotype being mistaken for *E. coli* O157:H7 is extremely remote. Requiring a positive result for each real-time assay as seen by a different detectable label on each probe for discrimination between each assay's amplification reaction provides a result that would be understood by the skilled artisan to be unambiguous, specific and sensitive for the detection of *E. coli* O157:H7.

The dual or multiplex (more than 2 assay sets) assay approach can be used to detect and distinguish other regional pathogenic *E. coli*. EHEC is identified as being caused by two classes of *E. coli*. Class 1 is predominant in the United States, caused by pathogenic strains of *E. coli* O157:H7 and Class 2 is more geographically dispersed and is caused by *E. coli* O26 and *E. coli* O111. As provided in Table 3, depending on the local beef population's indigenous *E. coli* and possible imported beef source, various pathogenic strains of *E. coli* are a public health threat.

TABLE 3

| Country/Continent | *E. coli* Serotye (s) | Class |
|---|---|---|
| United States | O157:H7 | 1 |
| South America | O26 and O111 | 2 |
| Scotland | O26 and O111 | 2 |
| Germany | O157:H7 and O26 | 1 & 2 |
| Australia | O26 and O111 | 2 |

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

The materials for use in the present invention are ideally suited for the preparation of a kit suitable for identifying the presence of *E. coli* O157:H7 and not *E. coli* O55:H7. Such a kit may comprise various reagents utilized in the methods, preferably in concentrated form. The reagents of this kit may comprise, but are not limited to, buffer, appropriate nucleotide triphosphates, DNA polymerases, intercalating dye, primers, probes, salt, and instructions for the use of the kit.

Those having ordinary skill in the art will understand that many modifications, alternatives, and equivalents are possible. All such modifications, alternatives, and equivalents are intended to be encompassed herein.

EXAMPLES

The following procedures are representative of procedures that can be employed for the detection of *E. coli* O157:H7.

Example 1

PCR Reaction Conditions to Evaluate O-Island Assays

All amplifications are done with "TrueAllele" PCR Master Mix
Primer pairs prepped at a [5 µM] each
Template is 1 µL of a 1→100 dilution of the bacterial lysate
Reaction Mix Preparation:

|  | Per reaction | for 50 reactions |
|---|---|---|
| True Allele MM | 18 µl | 900 µl |
| Primer mix 5 µM | 2 µl | 100 µl |
| ddH$_2$O | 9 µl | 450 µl | vortex briefly to mix components

Plate Preparation:
Pipette 1 µl of template from the template plate to reaction plate conserving well position.
Add 29 µl of Reaction Mix
Seal with adhesive cover, staking cover very well
Vortex briefly to mix components
Spin down plates and thermalcycle Thermal cycler profile: 95° C. 10'→95° C. 15"–60° C. 60" (×30 cycles)→4° C.

Example 2

Sequencing Reaction Protocol

Sequencing Reaction Mix:

|  | Per reaction | for 100 reactions |
|---|---|---|
| 5x sequencing buffer | 3.2 | 320 |
| BDT v.3.1 RR mix | 1.6 | 160 |
| Seq. primer 1 µM | 1.0 | 100 |
| ddH2O | 7.2 | 720 |
| total | 13 | 1300 |

1. Add 13 µl of above reaction mix to 7 µl of Exo-SAPped PCR amplicon, vortex, spin down and thermal cycle

Dye Exterminator Clean-Up of Sequencing Reactions Protocol

1. Prepare dye exterminator mix:
   82% SAM buffer
   18% Dye Exterminators beads (agitate before pipetting)
   For 96 sequences prepare 10 ml: 8.2 ml of SAM+1.8 ml of beads
2. For each 10 µl of sequencing reactions add 50 µl of Dye Exterminator mix: to each 20 µl reaction add 100 µl
3. Heat seal plates at 160° C. for 2 seconds
4. Vortex at ~1800 rpm for 30 minutes
5. Spin down in centrifuge at ~1000 rpm for 2 minutes
6. Load plates on sequencer and make sure to use appropriate Dye Exterminator module for injection While the foregoing specification teaches the principles of the present invention, with examples provided for the purpose of illustration, it will be appreciated by one skilled in the art from reading this disclosure that various changes in form and detail can be made without departing from the spirit and scope of the invention. These methods are not limited to any particular type of nucleic acid sample: plant, bacterial, animal (including human) total genome DNA, RNA, cDNA and the like may be analyzed using some or all of the methods disclosed in this invention. This invention provides a powerful tool for analysis of complex nucleic acid samples. From experiment design to detection of *E. coli* O157:H7 assay results, the above invention provides for fast, efficient and inexpensive methods for detection of pathogenic *E. coli* O157:H7.

All publications and patent applications cited above are incorporated by reference in their entirety for all purposes to the same extent as if each individual publication or patent application were specifically and individually indicated to be so incorporated by reference. Although the present invention has been described in some detail by way of illustration and example for purposes of clarity and understanding, it will be apparent that certain changes and modifications may be practiced within the scope of the appended claims.

The embodiments of the invention in which an exclusive property or privilege is claimed are defined as follows:

1. An assay for the detection of *E. coli* O157:H7 in a sample comprising:
    a) hybridizing a first pair of PCR primers to a first target polynucleotide sequence within SEQ ID NO:111;
    b) hybridizing a second pair of PCR primers to a second target polynucleotide sequence within a sequence selected from SEQ ID NO:91-110;
    c) amplifying said at least first and said at least second target polynucleotide sequences; and
    d) detecting said at least first and said at least second amplified target polynucleotide sequence products;
    wherein the detection of the at least first amplified target polynucleotide sequence product and the detection of the at least second amplified target polynucleotide sequence product is indicative of the presence of *E. coli* O157:H7 in the sample and not *E. coli* O55:H7.

2. The assay of claim 1, further comprising using a first probe having SEQ ID NO:3 to detect the at least first amplified target polynucleotide sequence product and using a second probe selected from SEQ ID NO:9, SEQ ID NO:12, SEQ ID NO:15, SEQ ID NO:18, SEQ ID NO:21, SEQ ID NO:24, SEQ ID NO:27 SEQ ID NO:30, SEQ ID NO:33, SEQ ID NO:36, SEQ ID NO:39, SEQ ID NO:42, SEQ ID NO:45, SEQ ID NO:48, SEQ ID NO:51, SEQ ID NO:54, SEQ ID NO:57, SEQ ID NO:58, SEQ ID NO:60, SEQ ID NO:63, SEQ ID NO:66, SEQ ID NO:69, SEQ ID NO:72, SEQ ID NO:75, SEQ ID NO:78, SEQ ID NO:81, SEQ ID NO:84, SEQ ID NO:87, and SEQ ID NO:90 to detect the second amplified target polynucleotide sequence product, wherein said first probe further comprises a first label and said second probe further comprises a second label.

3. The assay of claim 2, wherein the first and the second labels are selected from a dye, a radioactive isotope, a chemiluminescent label, and an enzyme.

4. The assay of claim 3, wherein the dye comprises a fluorescein dye, a rhodamine dye, or a cyanine dye.

5. The assay of claim 4, wherein the dye is a fluorescein dye.

6. The assay of claim 5, wherein said first probe is labeled with FAM™ dye and said second probe is labeled with VIC® dye.

7. The assay of claim 1, further comprising preparing the sample for PCR amplification prior to hybridizing comprising at least one of the following processes: (1) bacterial enrichment, (2) separation of bacterial cells from the sample, (3) cell lysis, and (4) total DNA extraction.

8. The assay of claim 1, wherein the sample comprises a food or a water sample.

9. The assay of claim 8, wherein the food sample comprises a selectively enriched food matrix.

10. The assay of claim 1, wherein said amplifying is by polymerase chain reaction.

11. The assay of claim 1, wherein said hybridizing and amplifying of said first pair of polynucleotide primers occurs in a first vessel and said hybridizing and amplifying of said second pair of polynucleotide primers occurs in a second vessel.

12. The assay of claim 1, wherein said hybridizing and amplifying of said first pair of polynucleotide primers and said hybridizing and amplifying of said second pair of polynucleotide primers occurs in a single vessel.

13. The assay of claim 10, wherein said detection is a real-time assay.

14. The assay of claim 13, wherein said real-time assay is a SYBR® Green dye assay or a TaqMan® assay.

15. A method for specifically detecting *E. coli* O157:H7, comprising:
    hybridizing at least a first pair of polynucleotide primers to at least a first target polynucleotide sequence,
    hybridizing at least a second pair of polynucleotide primers to at least a second target polynucleotide sequence,
    amplifying said at least first and said at least second target polynucleotide sequences, and
    detecting said at least first and said at least second amplified target polynucleotide sequence products,
wherein the detection of the at least first amplified target polynucleotide sequence product and the detection of the at least second amplified target polynucleotide sequence product is indicative of the presence of *E. coli* O157:H7 in a sample and not *E. coli* O55:H7,
wherein said first primer pair is selected from SEQ ID NO:1-2, SEQ ID NO:1 and SEQ ID NO:4, SEQ ID NO:1 and SEQ ID NO:5, and SEQ ID NO:1 and SEQ ID NO:6 and said second primer pair is selected from SEQ ID NO:7-8, SEQ ID NO:10-11, SEQ ID NO:13-14, SEQ ID NO:16-17, SEQ ID NO:19-20, SEQ ID NO:22-23, SEQ ID NO:25-26, SEQ ID NO:28-29, SEQ ID NO:31-32, SEQ ID NO:34-35, SEQ ID NO:37-38, SEQ ID NO:40-41, SEQ ID NO:43-44, SEQ ID NO:46-47, SEQ ID NO:49-50, SEQ ID NO:52-53, SEQ ID NO:55-56, SEQ ID NO:59 and SEQ ID NO:56, SEQ ID NO:61-62, SEQ ID NO:64-65, SEQ ID NO:67-68, SEQ ID NO:70-71, SEQ ID NO:73-74, SEQ ID NO:76-77, SEQ ID NO:79-80, SEQ ID NO:82-83, SEQ ID NO:85-86, and SEQ ID NO:88-89.

16. The method of claim 15, further comprising using one or more probes to detect the first and the second amplified target polynucleotide sequences wherein a probe to detect the at least first amplified target polynucleotide sequence is SEQ ID NO:3 and a probe to detect the at least second amplified target nucleic acid target polynucleotide is selected from SEQ ID NO:9, SEQ ID NO:12, SEQ ID NO:15, SEQ ID NO:18, SEQ ID NO:21, SEQ ID NO:24, SEQ ID NO:27 SEQ ID NO:30, SEQ ID NO:33, SEQ ID NO:36, SEQ ID NO:39, SEQ ID NO:42, SEQ ID NO:45, SEQ ID NO:48, SEQ ID NO:51, SEQ ID NO:54, SEQ ID NO:57, SEQ ID NO:58, SEQ ID NO:60, SEQ ID NO:63, SEQ ID NO:66, SEQ ID NO:69, SEQ ID NO:72, SEQ ID NO:75, SEQ ID NO:78, SEQ ID NO:81, SEQ ID NO:84, SEQ ID NO:87, and SEQ ID NO:90.

17. The method of claim 15, wherein said first target polynucleotide sequence is within SEQ ID NO:111 and said second target polynucleotide sequence is within the group selected from SEQ ID NO:91-110.

* * * * *